United States Patent

Masaki et al.

[11] 4,178,367
[45] Dec. 11, 1979

[54] PROSTAGLANDIN I$_2$ ANALOGUES

[75] Inventors: Hayashi Masaki, Takatsuki; Yoshinobu Arai, Toyonaka; Yoshitaka Konishi; Katsuichi Shimoji, both of Takatsuki; Shuichi Ohuchida, Kyoto; Hiroyuki Ito, Suita; Hirohisa Wakatsuka, Takatsuki, all of Japan

[73] Assignee: Ono Pharmaceutical Co. Ltd., Osaka, Japan

[21] Appl. No.: 878,571

[22] Filed: Feb. 16, 1978

[30] Foreign Application Priority Data

Feb. 21, 1977 [JP] Japan .................. 52/017141
Mar. 22, 1977 [JP] Japan .................. 52/030494

[51] Int. Cl.$^2$ ............... A61K 31/34; C07D 307/93
[52] U.S. Cl. ............................... 424/285; 542/429; 260/346.22; 536/103; 424/180
[58] Field of Search ............ 260/346.22; 542/429; 536/103; 424/285

[56] References Cited

FOREIGN PATENT DOCUMENTS 851122 8/1977 Belgium .
854463 11/1977 Belgium .

OTHER PUBLICATIONS

Johnson et al., J. Am. Chem. Soc., 99:12, Jun. 8, 1977, pp. 4182-4184.

Primary Examiner—John M. Ford
Assistant Examiner—Bernard Dentz
Attorney, Agent, or Firm—Stevens, Davis, Miller & Mosher

[57] ABSTRACT

Prostaglandin I$_2$ analogues of the formula:

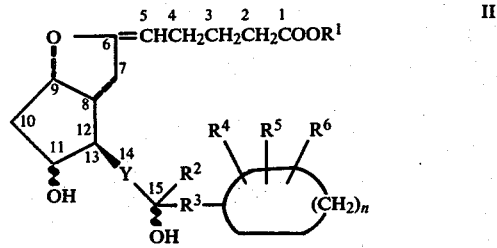

(wherein Y represents trans-vinylene or ethylene, $R^1$ represents hydrogen or an alkyl group containing from 1 to 12 carbon atoms, $R^2$ represents hydrogen, methyl or ethyl, $R^3$ represents a single bond, or an alkylene group containing from 1 to 4 carbon atoms, $R^4$, $R^5$ and $R^6$, which may be the same or different, each represent hydrogen or an alkyl group containing from 1 to 8 carbon atoms, n represents 3, 4, 5 or 6, the wavy line attached to the carbon atoms in positions 11 and 15 depicted in the formula represents α- or β-configuration or mixtures thereof, and the double bond between $C_6$-$C_6$ is Z or E) are new compounds possessing pharmacological properties typical of prostaglandins, for example PGI$_2$.

21 Claims, No Drawings

PROSTAGLANDIN I₂ ANALOGUES

This invention relates to new prostaglandin I$_2$ (PGI$_2$) analogoues, to a process for their preparation and pharmaceutical compositions containing them.

PGI$_2$ is a physiologically active substance having the following formula:

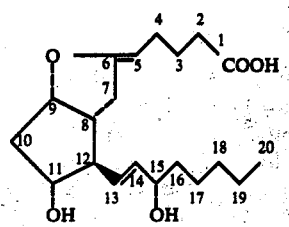

and its chemical name is (5Z,13E)-(9α,11α,15S)-6,9-epoxy-11,15-dihydroxyprosta-5,13-dienoic acid [Nature, 263, 663 (1976), Prostaglandins, 12, 685 (1976), ibid, 12, 915 (1976), ibid, 13, 3 (1977), ibid, 13, 375 (1977) and Chemical and Engineering News, Dec. 20, 17 (1976)].

It is well known that PGI$_2$ can be prepared by incubation of prostaglandin G$_2$ (PGG$_2$) or prostaglandin H$_2$ (PGH$_2$) with microsomal fractions prepared from thoracic aorta of swine, mesenteric artery of swine, rabbit aorta or the stomach fundus of rats. PGI$_2$ has a relaxing activity on the artery, which is peculiar to the artery and which does not operate on other smooth muscle. Furthermore, PGI$_2$ strongly inhibits arachidonic acid-induced blood platelet aggregation of the human.

Taking into consideration that thromboxane A$_2$ prepared by incubation of PGG$_2$ or PGH$_2$ with blood platelet microsome, has a contracting activity on the artery and an aggregating activity on blood platelets, the properties of PGI$_2$ heretofore mentioned show that PGI$_2$ fulfils a very important physiological part in a living body. PGI$_2$ may be useful in the treatment of arteriosclerosis, cardiac failure or thrombosis.

Widespread investigations have been carried out in order to discover processes for the chemical preparation of analogues of PGI$_2$ and (5E)-PGI$_2$, and their products possessing the pharmacological properties of the 'natural' PGI$_2$ or one of more of such properties to an enhanced degree, or hitherto unknown pharmacological properties. As a result of extensive research and experimentation a new process has been found and it has been discovered that by replacing the n-pentyl group at the end of the aliphatic group linked to the 12-position of the alicyclic ring of PGI$_2$ by a cycloalkyl group or an alkyl group substituted by a cycloalkyl group, the pharmacological properties of the 'natural' PGI$_2$ are, in some aspects of its activities, improved or modified.

The present invention accordingly provides new prostaglandin analogues of the general formula:

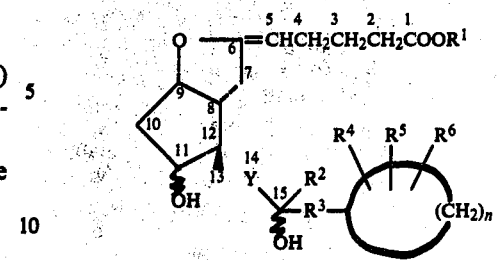

[wherein Y represents the trans-vinylene group (i.e.

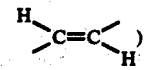)

or the ethylene group (i.e. —CH$_2$CH$_2$—), R$^1$ represents a hydrogen atom or a straight- or branched-chain alkyl group containing from 1 to 12, and preferably from 1 to 4, carbon atoms, R$^2$ represents a hydrogen atom or a methyl or ethyl group, R$^3$ represents a single bond, or a straight- or branched-chain alkylene group containing from 1 to 4 carbon atoms, R$^4$, R$^5$ and R$^6$, which may be the same or different, each represent a hydrogen atom or a straight- or branched-chain alkyl group containing from 1 to 8 carbon atoms, n represents 3, 4, 5 or 6, the wavy line ∿ attached to the carbon atoms in positions 11 and 15 depicted in formula II represents α- or β-configuration (i.e. S- or R-configuration) or mixtures thereof, and the double bond between C$_5$–C$_6$ is Z or E] and cyclodextrin clathrates of such acids and esters and, when R$^1$ represents a hydrogen atom, salts, more particularly non-toxic (e.g. sodium) salts thereof. Preferred compounds are those of general formula II wherein Y represents the trans-vinylene group, R$^1$ represents a hydrogen atom or a straight- or branched-chain alkyl group containing from 1 to 4 carbon atoms, especially methyl, R$^2$ represents a hydrogen atom and R$^4$, R$^5$ and R$^6$ each represent a hydrogen atom or one of the symbols R$^4$, R$^5$ and R$^6$ represents an alkyl group containing from 1 to 4 carbon atoms and the other two represent hydrogen atoms.

It is to be understood that the structure

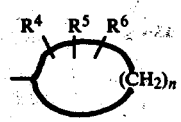

in general formula II and in subsequent formulae appearing in this specification represents an optionally substituted cyclobutyl, cyclopentyl, cyclohexyl or cycloheptyl group, and that one of the substituents R$^4$, R$^5$ and R$^6$ may be attached to the carbon atom by which the cycloalkyl group is attached to the symbol R$^3$.

The present invention is concerned with all compounds of general formula II in the 'natural' form or its enantiomeric form, or mixtures thereof, more particularly the racemic form, consisting of equimolecular mixtures of 'natural' form and its enantiomeric form.

As will be apparent to those skilled in the art, the compounds depicted in general formula II have at least five centres of chirality, these five centres of chirality being at the C-8, C-9, C-11, C-12 and C-15 carbon atoms. Still further centres of chirality may occur when $R^1$, $R^4$, $R^5$ or $R^6$ is a branched-chain alkyl group or $R^3$ is a branched-chain alkylene group. The presence of chirality leads as is well known to the existence of isomerism. However the compounds of general formula II all have such a configuration that the substituent groups attached to the ring carbon atoms in the positions identified as 8 and 12 are trans with respect to each other and that the substituent groups attached to the ring carbon atoms in the positions identified as 8 and 9 are cis with respect to each other.

Accordingly, all isomers of general formula II and mixtures thereof which have those substituent groups attached to the ring carbon atoms in positions 8 and 12 in the trans-configuration, those attached in positions 8 and 9 in the cis-configuration and have hydroxy groups as depicted in the 11- and 15-positions are to be considered within the scope of general formula II.

Preferably

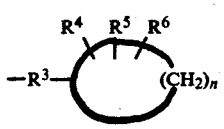

represents cyclobutyl, (1-propyl)cyclobutyl, (1-butyl)-cyclobutyl, (1-pentyl)cyclobutyl, (1-hexyl)cyclo butyl, (2-propyl)cyclobutyl, (3-ethyl)cyclobutyl, (3-propyl)-cyclobutyl, cyclopentyl, cyclopentylmethyl, 1-cyclopentylethyl, 2-cyclopentylethyl, 2-cyclopentyl-propyl, (3-ethyl)cyclopentyl, (3-propyl)cyclopentyl, (3-butyl)cyclopentyl, (1-methyl-3-propyl)cyclopentyl, (2-methyl-3-propyl)cyclopentyl, (2-methyl-4-propyl)-cyclopentyl, cyclohexyl, cyclohexylmethyl, 1-cyclohexylethyl, 2-cyclohexylethyl, (1-cyclohexyl-1-methyl)ethyl, (1-methyl-2-cyclohexyl)ethyl, 2-cyclohexylpropyl, 3-cyclohexylpropyl, (3-ethyl)cy-clohexyl, (4-methyl)cyclohexyl, (4-ethyl)cyclohexyl, (4-propyl)cyclohexyl, (2,6-dimethyl)cyclohexyl, (2,6-dimethyl-4-propyl)cyclohexyl, (1-methylcyclohexyl)-methyl, cycloheptyl, and of these, 1-cycloheptylethyl; 1-cyclopentylethyl, cyclohexyl, (trans-4-ethyl)cy-clohexyl, cyclohexylmethyl, 2-cyclohexylethyl, (3-propyl)cyclopentyl, (1-butyl)cyclobutyl and (1-methyl-2-cyclohexyl)ethyl are particularly preferred.

According to a feature of the present invention, the prostaglandin analogues of general formula II, wherein the double bond between $C_5$–$C_6$ is Z, and the other symbols are as hereinbefore defined, i.e. compounds of the general formula:

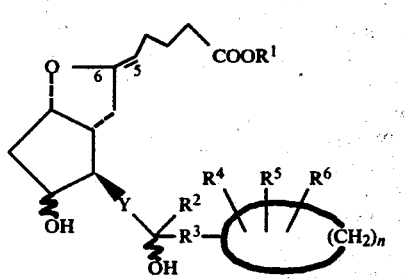

III (wherein the double bond between $C_5$–$C_6$ is Z, and the other symbols are as hereinbefore defined) are prepared by dehydrohalogenation of a compound of the general formula:

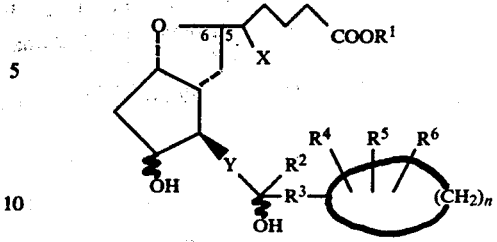

IV wherein X represents a bromine or iodine atom, the absolute configurations of $C_5$ and $C_6$ are (5R,6R) or (5S,6S) or a mixture thereof, and the other symbols are as hereinbefore defined.

The dehydrohalogenation may be carried out with a known dehydrohalogenation reagent, for example, (1) when X represents a bromine atom, a bicycloamine such as DBU (i.e. 1,5-diazabicyclo[5.4.0]undecene-5), DBN (i.e. 1,5-diazabicyclo[4.3.0]nonene-5) or DABCO (i.e. 1,4-diazabicyclo[2.2.2]octane), or an alkali metal, e.g. sodium or potassium, alcoholate containing from 1 to 4 carbon atoms, or (2) when X represents an iodine atom, a bicycloamine such as DBN, DBU or DABCO, or an alkali metal, e.g. sodium or potassium, alcoholate containing from 1 to 4 carbon atoms, superoxide, carbonate, hydroxide, benzoate, acetate, trifluoroacetate or bicarbonate, or silver acetate, or tetramethylammonium superoxide. The reaction may be carried out at a temperature from ambient to 110° C., preferably at a temperature from ambient to 80° C., and (1) when the reagent is a bicycloamine, optionally in the presence of an inert organic solvent, preferably in the absence of an inert organic solvent or in the presence of toluene or benzene, or (2) when the reagent is other than a bicycloamine, in the presence of an inert organic solvent, e.g. an alkanol containing from 1 to 4 carbon atoms, such as methanol or ethanol, or N,N-dimethylformamide.

When the reaction is carried out in the presence of a solvent, the reaction mixture may be concentrated under reduced pressure at a low temperature, e.g. at 0° to 5° C. after the reaction. The residue thus obtained or the reaction mixture obtained when the reaction is carried out in the absence of a solvent, may be adjusted, (1) when $R^1$ represents a hydrogen atom, to pH 5 to 7 or, (2) when $R^1$ represents an alkyl group, to pH 7 to 9 with an aqueous solution of an acid, e.g. dilute hydrochloric acid, and/or phosphate buffer, and extracted with an easily removable organic solvent such as diethyl ether. The extract, when $R^1$ represents a hydrogen atom, may be dried to give a solution of the $PGI_2$ analogue of general formula III. The extract, when $R^1$ represents an alkyl group, may be dried and concentrated under reduced pressure to give the $PGI_2$ analogue of general formula III. If desired, a product of general formula III, wherein $R^1$ represents an alkyl group, may be purified by thin layer or column chromatography on silica gel or magnesium silicate pretreated with triethylamine to give the pure $PGI_2$ analogue.

Compounds of general formula IV, wherein the various symbols are as hereinbefore defined, may be prepared by hydrolysis to a hydroxy group of the group $OR^7$ and, when $R^8$ is other than a hydrogen atom, of the group $OR^8$ of a compound of the general formula:

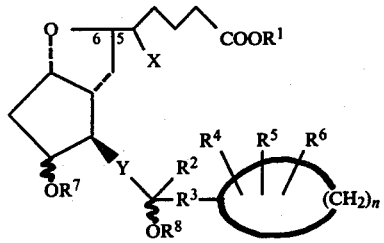

wherein R⁷ represents a tetrahydropyran-2-yl group unsubstituted or substituted by at least one alkyl group, or a tetrahydrofuran-2-yl or 1-ethoxyethyl group, $R^8$ represents a hydrogen atom, or a tetrahydropyran-2-yl group unsubstituted or substituted by at least one alkyl group, or a tetrahydrofuran-2-yl or 1-ethoxyethyl group, the absolute configurations of $C_5$ and $C_6$ are (5R,6R) or (5S,6S) or a mixture thereof, and other symbols are as hereinbefore defined.

The groups $OR^7$ and $OR^8$ (when $R^8$ is other than a hydrogen atom) of the compounds of general formula V may be converted to hydroxy groups by mild acidic hydrolysis (1) with an aqueous solution of an organic acid such as acetic acid, propionic acid, oxalic acid, or p-toluenesulphonic acid, or an aqueous solution of an inorganic acid such as hydrochloric, sulphuric or phosphoric acid, advantageously in the presence of an inert organic solvent miscible with water, e.g. a lower alkanol such as methanol or ethanol, preferably methanol, or an ether such as 1,2-dimethoxyethane, dioxan, or tetrahydrofuran (preferably tetrahydrofuran), at a temperature ranging from ambient to 75° C. (preferably at a temperature below 45° C.), or (2) with an anhydrous solution of an organic acid such as p-toluenesulphonic acid or trifluoroacetic acid in a lower alkanol such as methanol or ethanol at a temperature ranging from 10° to 45° C. Advantageously the mild acidic hydrolysis may be carried out with a mixture of dilute hydrochloric acid and tetrahydrofuran, a mixture of dilute hydrochloric acid and methanol, a mixture of acetic acid, water and tetrahydrofuran, a mixture of phosphoric acid, water and tetrahydrofuran, or a mixture of p-toluenesulphonic acid and methanol.

Compounds of general formula IV and V, i.e. compounds of the general formula:

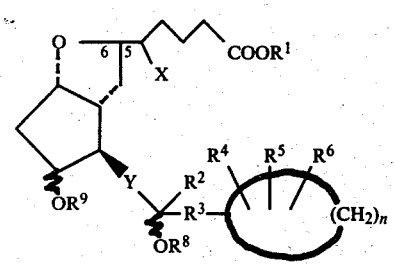

[wherein $R^9$ represents a hydrogen atom, or a tetrahydropyran-2-yl group unsubstituted or substituted by at least one alkyl group, or a tetrahydrofuran-2-yl or 1-ethoxyethyl group, the absolute configurations at $C_5$ and $C_6$ are (5R,6R) or (5S,6S) or a mixture thereof, and the other symbols are as hereinbefore defined], may be prepared by bromination or iodination, and simultaneous cyclisation, of a compound of the general formula:

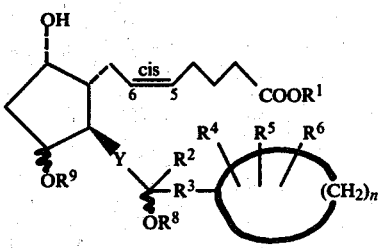

wherein the double bond between $C_5$–$C_6$ is cis and the various symbols are as hereinbefore defined.

The conversion of a compound of general formula VII to a compound of general formula VI may be suitably carried out, (1) when X in the compound of formula VI represents a bromine atom, with N-bromosuccinimide or N-bromoacetamide in an aprotic organic solvent, e.g. methylene chloride, chloroform, carbon tetrachloride, diethyl ether, N,N-dimethylformamide or tetrahydrofuran, or a mixture of two or more of them, at a temperature of from −30° to 70° C., or (2) when X in the compound of formula VI represents an iodine atom, with (i) iodine in pyridine, (ii) potassium periodate and potassium iodide in aqueous acetic acid, (iii) iodine and potassium iodide in the presence of an alkali metal, e.g. sodium or potassium, carbonate or bicarbonate in water, or (iv) iodine in the presence of an alkali metal, e.g. sodium or potassium, carbonate in an inert organic solvent, e.g. methylene chloride or chloroform, at a temperature of from ambient to 0° C. The product of general formula VI, thus obtained, is a mixture of isomers in which the absolute configurations of $C_5$ and $C_6$ are (5R,6R) and (5S,6S). If desired, the mixture may be separated by column, thin layer or high-speed liquid chromatography on silica gel to give each of the isomers. Each isomer or the mixture of isomers may be converted to the desired PGI₂ analogues of general formula III as described above.

The methods hereinbefore described for the preparation of PGI₂ analogues of general formula III may be represented by the series of reactions depicted schematically below in Scheme A, wherein the various symbols are as hereinbefore defined, the absolute configurations at $C_5$ and $C_6$ in formulae IV and V are (5R,6R) or (5S,6S) or a mixture thereof and the double bond between $C_5$–$C_6$ in formula III is Z.

SCHEME A

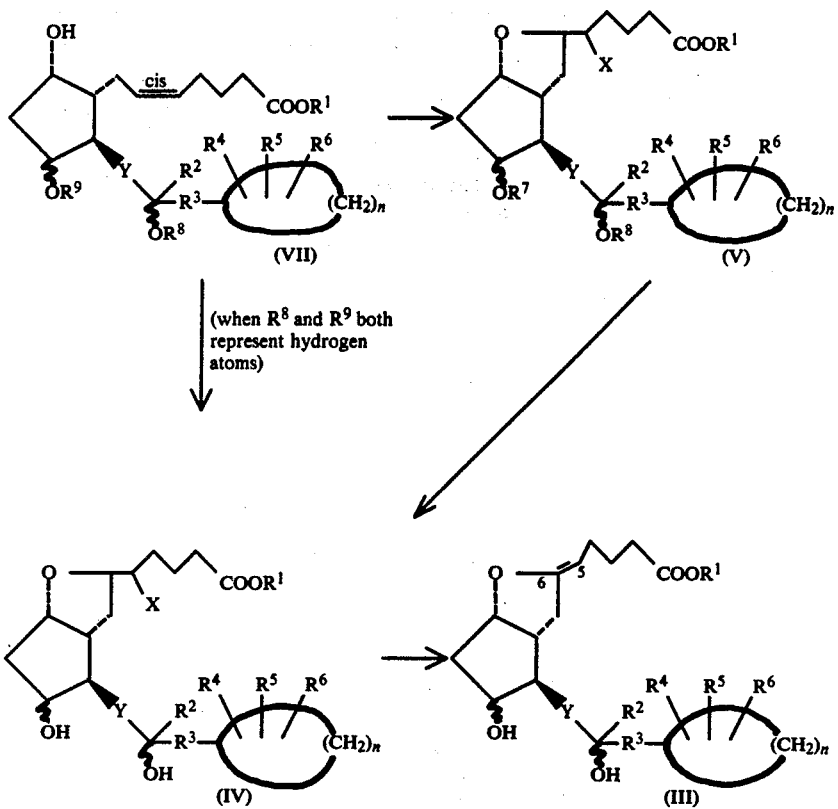

According to another features of the present invention, the prostaglandin analogues of general formula II, wherein the double bond between $C_5$–$C_6$ is E, and the other symbols are as hereinbefore defined, i.e. compounds of the general formula:

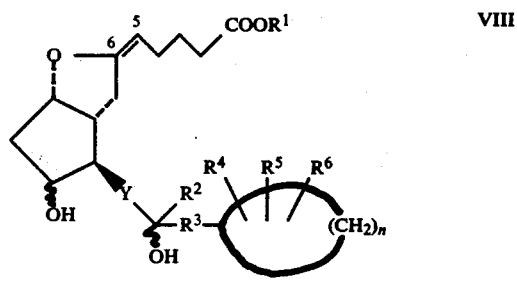

(wherein the double bond between $C_5$–$C_6$ is E, and the other symbols are as hereinbefore defined), are prepared by dehydrohalogenation of a compound of the general formula:

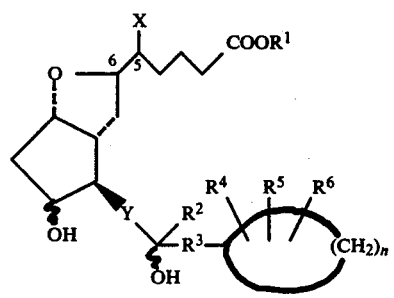

[wherein the absolute configurations of $C_5$ and $C_6$ are (5R,6S) or (5S,6R) or a mixture thereof, and the various symbols are as hereinbefore defined] by means heretofore mentioned for the conversion of compounds of general formula IV to those of general formula III.

Compounds of general formula IX may be prepared from a compound of the general formula:

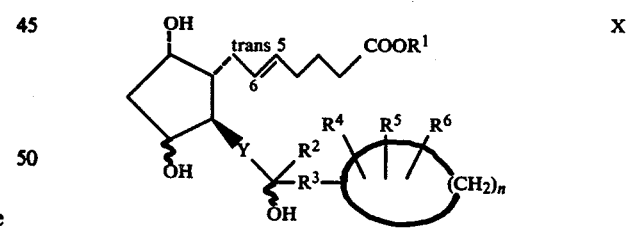

(wherein the double bond between $C_5$–$C_6$ is trans and the various symbols are as hereinbefore defined) by means heretofore mentioned for the conversion of compounds of general formula VII to those of general formula VI. The product of general formula IX, thus obtained, is a mixture of isomers in which the absolute configurations of $C_5$ and $C_6$ are (5R,6S) and (5S,6R). If desired, the mixture may be separated by column, thin layer or high-speed liquid chromatography on silica gel to give each of the isomers. Each isomer or the mixture of isomers may be converted to the desired $PGI_2$ analogues of general formula III as described above.

Compounds of general formula X may be prepared by photoisomerization of compounds of general formula VII, wherein $R^8$ and $R^9$ both represent hydrogen atoms, and the other symbols are as hereinbefore defined, i.e. compounds of the general formula:

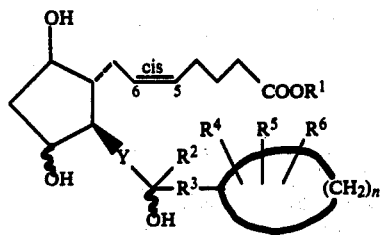
VIIA (wherein the various symbols are as hereinbefore defined) with light from a high pressure mercury lamp in the presence of diphenyl sulphide or diphenyl disulphide in an inert organic solvent, e.g a mixture of benzene and methanol, at room temperature. The product obtained may be purified by column or high layer chromatography on silica gel pretreated with silver nitrate to give compounds of general formula X.

The methods hereinbefore described for the preparation of (5E)-PGI$_2$ analogues of general formula VIII may be represented by the series of reactions depicted schematically below in Scheme B, wherein the various symbols are as hereinbefore defined, the absolute configurations at C$_5$ and C$_6$ in formula IX are (5R,6S) or (5S,6R) or a mixture thereof, and the double bond between C$_5$–C$_6$ in formula VIII is E.

4,034,003, 4,024,174 and 4,045,468, U.S. application Ser. No. 703,158 and Belgian Pat. No. 844,256.

In particular, starting materials of general formula VII may be prepared by the synthetic routes described in the above-mentioned patent specifications and applications, using as a starting material a phosphonate of the general formula:

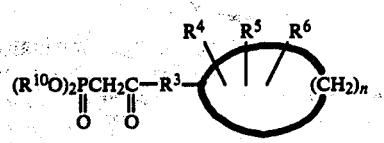
XI (wherein R$^{10}$ represents an alkyl group containing from 1 to 4 carbon atoms, and the other symbols are as hereinbefore defined) or a Grignard reagent of the general formula:

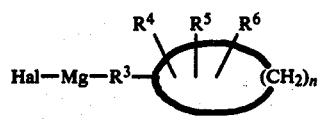
XII wherein Hal represents a halogen atom, and the other symbols are as hereinbefore defined.

The phosphonates of general formula XI, wherein the various symbols are as hereinbefore defined, may be prepared by reacting a solution of n-butyllithium in an

SCHEME B

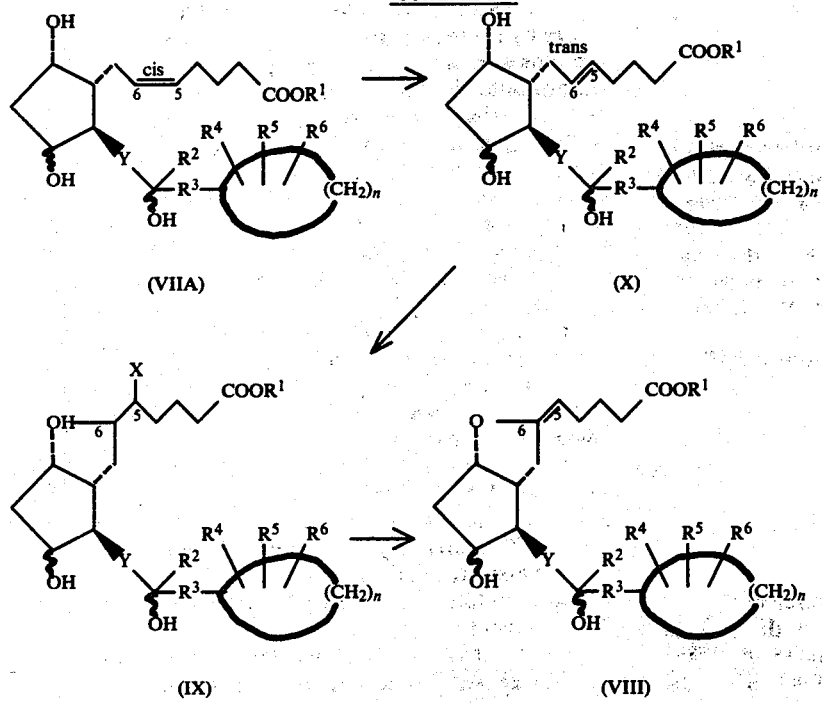

Starting materials of general formula VII may be prepared by the methods described in the following patent specifications and applications, or obvious modifications thereof: Japanese Patent Kokai Nos. 50-13364, 50-25549, 50-148339 and 51-68547, Japanese Patent Application No. 52-88919, British Patent Specifications Nos. 1,450,691, 1,464,916, 1,488,141, 1,483,240 and 1,484,210, British Patent Applications Nos. 30072/75 and 18651/76, U.S. Pat. Nos. 3,962,312, 3,966,792, inert organic solvent, e.g. n-hexane, diethyl ether or tetrahydrofuran, with a solution of a dialkyl methylphosphonate of the general formula:

XIII (wherein R$^{10}$ is as hereinbefore defined), e.g. dimethyl methylphosphonate or diethyl methylphosphonate, at a temperature below −50° C., and then adding to the reaction mixture a solution of a compound of the general formula:

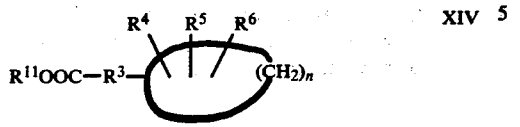

(wherein $R^{11}$ represents an alkyl group containing from 1 to 4 carbon atoms, and the other symbols are as hereinbefore defined) in an inert organic solvent, e.g. tetrahydrofuran, at a temperature below −50° C., and stirring at a moderately low temperature, e.g. at 0° C., to give the desired phosphonate of general formula XI.

The phosphonates of general formula XI, wherein $R^3$ is other than a single bond, may also be prepared by reaction of a dianion compound of the general formula:

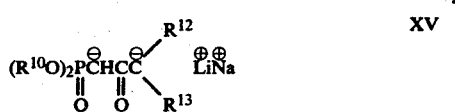

(wherein $R^{12}$ and $R^{13}$, which may be the same or different, each represents a hydrogen atom or a straight- or branched-chain alkyl group containing from 1 to 3 carbon atoms, and $R^{10}$ is as hereinbefore defined) with a halogen compound of the general formula:

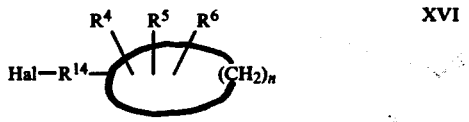

(wherein $R^{14}$ represents a single bond or a straight- or branched-chain alkylene group containing from 1 to 3 carbon atoms, but the total number of carbon atoms in $R^{12}$, $R^{13}$ and $R^{14}$ is not more than 3, and the other symbols are as hereinbefore defined) in an inert organic solvent, e.g. tetrahydrofuran, n-hexane, n-pentane, diethyl ether, or a mixture of two or more of them, at or below room temperature.

The dianion compound of general formula XV may be prepared by treatment of a compound of the general formula:

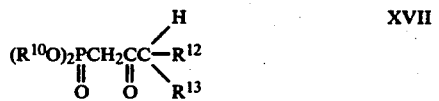

(wherein the various symbols are as hereinbefore defined) with sodium hydride and n-butyllithium in an inert organic solvent, e.g. tetrahydrofuran, n-hexane, n-pentane, diethyl ether, or a mixture of two or more of them, at or below room temperature.

The Grignard reagent of general formula XII may be prepared by methods known per se from the corresponding halogen compound. The compounds of general formulae XIV and XVI may also be prepared by methods known per se.

By the term "methods known per se" as used in this specification is meant methods heretofore used or described in the chemical literature.

The compounds of general formulae IV and IX wherein X represents an iodine atom and the other symbols are as hereinbefore defined are new compounds and as such constitute a further feature of the present invention.

Esters of the prostaglandin analogues of general formula II, i.e. compounds of general formula II wherein $R^1$ represents a straight- or branched-chain alkyl group containing from 1 to 12 carbon atoms and the other symbols are as hereinbefore defined, may be prepared by esterification of the corresponding acid of general formula II wherein $R^1$ represents a hydrogen atom by methods known per se (i.e. methods heretofore used or described in the chemical literature), for example by reaction with the appropriate diazoalkane in an inert organic solvent, e.g. diethyl ether, at a temperature of from −10° to 25° C. and preferably 0° C.

Compounds of general formula II wherein $R^1$ represents a hydrogen atom may, if desired, be converted by methods known per se into salts. Preferably the salts are non-toxic salts. By the term 'non-toxic salts', as used in this specification, is meant salts the cations of which are relatively innocuous to the animal organism when used in therapeutic doses so that the beneficial pharmacological properties of the compounds of general formula II are not vitiated by side-effects ascribable to those cations. Preferably the salts are water-soluble. Suitable non-toxic salts include the alkali metal, e.g. sodium or potassium, salts, the alkaline earth metal, e.g. calcium or magnesium, salts and ammonium salts, and pharmaceutically acceptable, (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms. Suitable non-toxic amine salts are, e.g. tetraalkylammonium, such as tetramethylammonium, salts, and other organic amine salts such as methylamine salts, dimethylamine salts, cyclopentylamine salts, benzylamine salts, phenethylamine salts, piperidine salts, monoethanolamine salts, diethanolamine salts, lysine salts or arginine salts.

Salts may be prepared from the acids of general formula II wherein $R^1$ represents a hydrogen atom, by methods known per se, for example by reaction of stoichiometric quantities of an acid of general formula II and the appropriate base, e.g. an alkali metal or alkaline earth metal hydroxide or carbonate, ammonium hydroxide, ammonia or an organic amine, in a suitable solvent. The salts may be isolated by lyophilisation of the solution or, if sufficiently insoluble in the reaction medium, by filtration, if necessary after removal of part of the solvent.

Sodium salts may also be prepared by treatment of an ester of general formula II, wherein $R^1$ represents an alkyl group containing from 1 to 12 carbon atoms, and the other symbols are as hereinbefore defined, with one equivalent amount of sodium hydroxide in the presence of an aqueous alkanol containing from 1 to 4 carbon atoms, preferably aqueous methanol, at a temperature of from 0° to 60° C., preferably at ambient temperature.

Cyclodextrin clathrates of the prostaglandin analogues of general formula II may be prepared by dissolving the cyclodextrin in water or an organic solvent which is miscible with water in the presence of triethylamine and adding to the solution the prostaglandin analogue in a water-miscible organic solvent. The mixture is then heated and the desired cyclodextrin clathrate product isolated by concentrating the mixture under reduced pressure, or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. α, β- or γ-Cyclodextrins or mixtures thereof may be used in the preparation of the cyclodextrin clathrates. Conversion into cyclodextrin clathrates serves to increase the stability of the prostaglandin analogues.

The prostaglandin analogues of general formula II and their cyclodextrin clathrates, and when $R^1$ represents a hydrogen atom, non-toxic salts possess the valuable pharmacological properties typical of the prostaglandins in a selective fashion, in particular hypotensive activity, inhibitory activity on blood platelet aggregation, relaxing activity of artery, inhibitory activity on gastric acid secretion and gastric ulceration, stimulatory activity on uterine contraction and abortifacient, luteolytic and antinidatory activity, and are useful in the treatment of hypertension, in the treatment of disorders of the peripheral circulation, in the prevention and treatment of cerebral thrombosis, myocardial infarction and arteriosclerosis, in the treatment of gastric ulceration, in the termination of pregnancy and induction of labour in pregnant female mammals and in the treatment of impaired fertility, in the control of oestrus, contraception and menstrual regulation in female mammals.

For example, in standard laboratory tests, (i) by intravenous administration to the allobarbital-anaesthetized dog, (5Z,13E)-(9α,11α,15S)-6,9-epoxy-11,15-dihydroxy-15-(3-propyl)cyclopentyl-16,17,18,19,20-pentanorprosta-5,13-dienoic acid methyl ester produces a fall in blood pressure of 12 mmHg and 50 mmHg lasting 9, 14 and 16 minutes at the doses of 0.05, 0.1 and 0.2 μg/kg animal body weight, respectively, (5Z,13E)-(9α,11α,15R)-6,9-epoxy-11,15-dihydroxy-15-(1-butyl)-cyclobutyl-16,17,18,19,20-pentanorprosta-5,13-dienoic acid methyl ester produces a fall in blood pressure of 12 mmHg and 40 mmHg lasting 3 and 10 minutes at the doses of 2 and 5 μg/kg animal body weight, respectively, (5Z,13E)-(9α,11α,15S,16RS)-6,9-epoxy-11,15-dihydroxy-16-cyclopentyl-18,19,20-trinorprosta-5,13-dienoic acid methyl ester produces a fall in blood pressure of 20 mmHg and 54 mmHg lasting 13 and 22 minutes at the doses of 0.3 and 1.0 μg/kg animal body weight, respectively, (5Z,13E)-(9α,11α,15S)-6,9-epoxy-11,15-dihydroxy-15-cyclohexyl-16,17,18,19,20-pentanorprosta-5,13-dienoic acid methyl ester produces a fall in blood pressure of 16 mmHg and 30 mmHg lasting 6 and 8 minutes at the doses of 0.2 and 0.5 μg/kg animal body weight, respectively, (5Z,13E)-(9α,11α,15S)-6,9-epoxy-11,15-dihydroxy-15-(3-propyl)cyclopentyl-16,17,18,19,20-pentanorprosta-5,13-dienoic acid sodium salt produces a fall in blood pressure of 23 mmHg and 35mmHg lasting 11 and 15 minutes at the doses of 0.1 and 0.2 μg/kg animal body weight, respectively, (5Z,13E)-(9α,11α15S)-6,9-epxoy-11,15-dihydroxy-15-(trans-4-ethyl)cyclohexyl-16,17,18,19,20-pentanorprosta-5,13-dienoic acid methyl ester produces a fall in blood pressure of 24 mmHg and 50 mmHg lasting 10 and 17 minutes at the doses of 1 and 2 μg/kg animal body weight, respectively, (5Z,13E)-(9α,11α,15S)-6,9-epoxy-11,15-dihydroxy-16-cyclohexyl-17,18,19,20-tetranorprosta-5,13-dienoic acid methyl ester produces a fall in blood pressure of 18 mmHg and 48 mmHg lasting 7 and 14 minutes at the doses of 0.5 and 1.0 μg/kg animal body weight, respectively, (5Z,13E)-(9α,1 1α,15S,16RS)-6,9-epoxy-11,15-dihydroxy-16-methyl-17-cyclohexyl-18,19,20-trinorprosta-5,13-dienoic acid methyl ester produces a fall in blood pressure of 26 mmHg and 46 mmHg lasting 10 and 15 minutes at the doses of 0.5 and 1.0 μg/kg animal body weight, respectively, and (5Z,13E)-(9α,11α,15S)-6,9-epoxy-11,15-dihydroxy-17-cyclohexyl-18,19,20-trinorprosta-5,13-dienoic acid methyl ester produces a fall in blood pressure of 22 mmHg and 44 mmHg lasting 8 and 13 minutes at the doses of 2 and 5 μg/kg animal body weight, respectively, (ii) (5Z,13E)-(9α,11α,15S)-6,9-epoxy-11,15-dihydroxy-15-(3-propyl)cyclopentyl-16,17,18,19,20-pentanorprosta-5,13-dienoic acid methyl ester, (5Z,13E)-(9α,11α,15R)-6,9-epoxy-11,15-dihydroxy-15-(1-butyl)-cyclobutyl-16,17,18,19,20-pentanorprosta-5,13-dienoic acid methyl ester, (5Z,13E)-(9α,1 1α,15S,16RS)-6,9-epoxy-11,15-dihydroxy-16-cyclohexyl-18,19,20-trinorprosta-5,13-dienoic acid methyl ester, (5Z,13E)-(9α,11α,15S)-6,9-epoxy-11,15-dihydroxy-15-cyclohexyl-16,17,18,19,20-pentanorprosta-5,13-dienoic acid methyl ester, (5Z,13E)-(9α,11α,15S)-6,9-epoxy-11,15-dihydroxy-15-(3-propyl)cyclopentyl-16,17,18,19,20-pentanorprosta-5,13-dienoic acid sodium salt, (5Z,13E)-(9α,11α,15S)-6,9-epoxy-11,15-dihydroxy-15-(trans-4-ethyl)cyclohexyl-16,17,18,19,20-pentanorprosta-5,13-dienoic acid methyl ester, (5Z,13E)-(9α,1 1α,15S)-6,9-epoxy-11,15-dihydroxy-16-cyclohexyl-17,18,19,20-tetranorprosta-5,13-dienoic acid methyl ester, (5Z,13E)-(9α,11α,15S,16RS)-6,9-epoxy-11,15-dihydroxy-16-methyl-17-cyclohexyl-18,19,20-trinorprosta-5,13-dienoic acid methyl ester and (5Z,13E)-(9α,1 1α,15S)-6,9-epoxy-11,15-dihydroxy-17-cyclohexyl-18,19,20-trinorprosta-5,13-dienoic acid methyl ester produce a 50% inhibition of adenosine diphosphate-induced blood platelet aggregation in platelet-rich plasma of rats at the concentrations of $1.35 \times 10^{-3}$, $4.2 \times 10^{-3}$, $7.8 \times 10^{-3}$, $1.7 \times 10^{-3}$, $9.0 \times 10^{-4}$, $8.5 \times 10^{-4}$, $4.7 \times 10^{-3}$, $5.8 \times 10^{-2}$ and $1.4 \times 10^{-2}$ μg/ml, respectively, in comparison with controls, and (iii) (5Z,13E)-(9α,11α,15R)-6,9-epoxy-11,15-dihydroxy-15-(1-butyl)cyclobutyl-16,17,18,19,20-pentanorprosta-5,13-dienoic acid methyl ester stimulates uterine contraction in the pregnant female rat when administered intravenously on the 20th day of gestation at doses of 5–10 μg/kg animal body weight.

Preferred PGI$_2$ analogues of the present invention are as follows:
15-cyclobutyl-16,17,18,19,20-pentanor-PGI$_2$,
15-(1-propyl)cyclobutyl-16,17,18,19,20-pentanor-PGI$_2$,
15-(1-butyl)cyclobutyl-16,17,18,19,20-pentanor-PGI$_2$,
15-(1-pentyl)cyclobutyl-16,17,18,19,20-pentanor-PGI$_2$,
15-(1-hexyl)cyclobutyl-16,17,18,19,20-pentanor-PGI$_2$,
15-(2-propyl)cyclobutyl-16,17,18,19,20-pentanor-PGI$_2$,
15-(3-ethyl)cyclobutyl-16,17,18,19,20-pentanor-PGI$_2$),
15-(3-propyl)cyclobutyl-16,17,18,19,20-pentanor-PGI$_2$,
15-cyclopentyl-16,17,18,19,20-pentanor-PGI$_2$,
16-cyclopentyl-18,19,20-trinor-PGI$_2$,
17-cyclopentyl-18,19,20-trinor-PGI$_2$,
17-cyclopentyl-19,20-dinor-PGI$_2$,
15-(3-ethyl)cyclopentyl-16,17,18,19,20-pentanor-PGI$_2$,
15-(3-propyl)cyclopentyl-16,17,18,19,20-pentanor-PGI$_2$,
15-(3-butyl)cyclopentyl-16,17,18,19,20-pentanor-PGI$_2$, 15-(1-methyl-3-propyl)cyclopentyl-16,17,18,19,20-pentanor-PGI$_2$,
15-(2-methyl-3-propyl)cyclopentyl-16,17,18,19,20-pentanor-PGI$_2$,
15-(2-methyl-4-propyl)cyclopentyl-16,17,18,19,20-pentanor-PGI$_2$,
15-cyclohexyl-16,17,18,19,20-pentanor-PGI$_2$,
15-(3-ethyl)cyclohexyl-16,17,18,19,20-pentanor-PGI$_2$,
15-(4-methyl)cyclohexyl-16,17,18,19,20-pentanor-PGI$_2$,
15-(4-ethyl)cyclohexyl-16,17,18,19,20-pentanor-PGI$_2$,
15-(4-propyl)cyclohexyl-16,17,18,19,20-pentanor-PGI$_2$,
15-(2,6-dimethyl)cyclohexyl-16,17,18,19,20-pentanor-PGI$_2$,
15-(2,6-dimethyl-4-propyl)cyclohexyl-16,17,18,19,20-pentanor-PGI$_2$,
16-cyclohexyl-17,18,19,20-tetranor-PGI$_2$,
16-(1-methyl)cyclohexyl-17,18,19,20-tetranor-PGI$_2$,
16-cyclohexyl-18,19,20-trinor-PGI$_2$,
17-cyclohexyl-18,19,20-trinor-PGI$_2$,
16-cyclohexyl-16-methyl-18,19,20-trinor-PGI$_2$,
16-methyl-17-cyclohexyl-18,19,20-trinor-PGI$_2$,
17-cyclohexyl-19,20-dinor-PGI$_2$,
18-cyclohexyl-19,20-dinor-PGI$_2$,
16-cycloheptyl-18,19,20-trinor-PGI$_2$,
15-cycloheptyl-16,17,18,19,20-pentanor-PGI$_2$,
15-cyclobutyl-13,14-dihydro-16,17,18,19,20-pentanor-PGI$_2$,
15-(1-propyl)cyclobutyl-13,14-dihydro-16,17,18,19,20-pentanor-PGI$_2$,
15-(1-butyl)cyclobutyl)-13,14-dihydro-16,17,18,19,20-pentanor-PGI$_2$,
15-(1-pentyl)cyclobutyl-13,14-dihydro-16,17,18,19,20-pentanor-PGI$_2$,
15-(1-hexyl)cyclobutyl-13,14-dihydro-16,17,18,19,20-pentanor-PGI$_2$,
15-(2-propyl)cyclobutyl-13,14-dihydro-16,17,18,19,20-pentanor-PGI$_2$,
15-(3-ethyl)cyclobutyl-13,14-dihydro-16,17,18,19,20-pentanor-PGI$_2$,
15-(3-propyl)cyclobutyl-13,14-dihydro-16,17,18,19,20-pentanor-PGI$_2$,
15-cyclopentyl-13,14-dihydro-16,17,18,19,20-pentanor-PGI$_2$
16-cyclopentyl-13,14-dihydro-18,19,20-trinor-PGI$_2$,
17-cyclopentyl-13,14-dihydro-18,19,20-trinor-PGI$_2$,
17-cyclopentyl-13,14-dihydro-19,20-dinor-PGI$_2$,
15-(3-ethyl)cyclopentyl-13,14-dihydro-16,17,18,19,20-pentanor-PGI$_2$,
15-(3-propyl)cyclopentyl-13,14-dihydro-16,17,18,19,20-pentanor-PGI$_2$,
15-(3-butyl)cyclopentyl-13,14-dihydro-16,17,18,19,20-pentanor-PGI$_2$,
15-(1-methyl-3-propyl)cyclopentyl-13,14-dihydro-16,17,18,19,20-pentanor-PGI$_2$,
15-(2-methyl-3-propyl)cyclopentyl-13,14-dihydro-16,17,18,19,20-pentanor-PGI$_2$,
15-(2-methyl-4-propyl)cyclopentyl-13,14-dihydro-16,17,18,19,20-pentanor-PGI$_2$,
15-cyclohexyl-13,14-dihydro-16,17,18,19,20-pentanor-PGI$_2$,
15-(3-ethyl)cyclohexyl-13,14-dihydro-16,17,18,19,20-pentanor-PGI$_2$,
15-(4-methyl)cyclohexyl-13,14-dihydro-16,17,18,19,20-pentanor-PGI$_2$,
15-(4-ethyl)cyclohexyl-13,14-dihydro-16,17,18,19,20-pentanor-PGI$_2$,
15-(4-propyl)cyclohexyl-13,14-dihydro-16,17,18,19,20-pentanor-PGI$_2$,
15-(2,6-dimethyl)cyclohexyl-13,14-dihydro-16,17,18,19,20-pentanor-PGI$_2$,
15-(2,6-dimethyl-4-propyl)cyclohexyl-13,14-dihydro-16,17,18,19,20-pentanor-PGI$_2$,
16-cyclohexyl-13,14-dihydro-17,18,19,20-tetranor-PGI$_2$,
16-(1-methyl)cyclohexyl-13,14-dihydro-17,18,19,20-tetranor-PGI$_2$,
16-cyclohexyl-13,14-dihydro-18,19,20-trinor-PGI$_2$,
17-cyclohexyl-13,14-dihydro-18,19,20-trinor-PGI$_2$,
16-cyclohexyl-16-methyl-13,14-dihydro-18,19,20-trinor-PGI$_2$,
16-methyl-17-cyclohexyl-13,14-dihydro-18,19,20-trinor-PGI$_2$,
17-cyclohexyl-13,14-dihydro-19,20-dinor-PGI$_2$,
18-cyclohexyl-13,14-dihydro-19,20-dinor-PGI$_2$,
16-cycloheptyl-13,14-dihydro-18,19,20-trinor-PGI$_2$,
15-cycloheptyl-13,14-dihydro-16,17,18,19,20-pentanor-PGI$_2$, and the corresponding (5E)-PGI$_2$ analogues, corresponding 15-methyl- and 15-ethyl-PGI$_2$ and (5E)-PGI$_2$ analogues, alkyl esters thereof, cyclodextrin clathrates of the PGI$_2$ and (5E)-PGI$_2$ and 15-methyl- and 15-ethyl-PGI$_2$ and (5E)-PGI$_2$ analogues and their esters, and non-toxic salts of the PGI$_2$ and (5E)-PGI$_2$ and 15-methyl- and 15-ethyl-PGI$_2$ and (5E)-PGI$_2$ analogues.

In the following Reference Examples and Examples it is to be understood that compounds in which the configurations at the 5- and 6-position carbon atoms are given as 5R,S, 6R,S are a mixture of the 5R,6R and 5S,6S isomers of those compounds.

The following Reference Examples and Examples illustrate, but not limit, the preparation of new prostaglandin I$_2$ analogues of the present invention. In them 'TLC', 'IR' and 'NMR' represent respectively 'Thin layer chromatography', 'Infrared absorption spectrum' and 'Nuclear magnetic resonance spectrum'. Where solvent ratios are specified in chromatographic separation, the ratios are by volume.

REFERENCE EXAMPLE 1

Dimethyl 2-oxo-3RS-methyl-4-cyclohexylbutylphosphonate

Under an atmosphere of nitrogen, a solution of 7.20 g of dimethyl 2-oxobutylphosphonate in 60 ml of tetrahydrofuran was added dropwise to a suspension of 960 mg of sodium hydride in 100 ml of tetrahydrofuran at room temperature and the mixture was stirred for 30 minutes. To the solution thus obtained was added dropwise 34 ml of a 1.25M solution of n-butyllithium in n-hexane at 0° C., the mixture was stirred until the solution became clear, and then 7.75 g of cyclohexylmethyl bromide were added dropwise and the mixture was stirred for 30 minutes at the same temperature. The reaction mixture was acidified to pH 4 with 5% w/v hydrochloric acid and concentrated under reduced pressure. The residue was diluted with ethyl acetate, washed with water and an aqueous solution of sodium chloride, dried over magnesium sulphate and concentrated under reduced pressure. The residue was purified by column chromatography on silica gel using benzene as eluent to give 10.6 g of the title compound having the following physical characteristics:

IR (liquid film): ν; 2930, 2855, 1715, 1450, 1265, 1035 cm$^{-1}$;

NMR (CCl₄ solution): δ; 3.72 (6H, d), 3.00 (2H, d), 2.95-2.65 (1H, m), 1.06 (3H, d).

REFERENCE EXAMPLE 2

(5Z,13E)-(9α,11α,16RS)-9-Acetoxy-11-(tetrahydropyran-2-yloxy)-15-oxo-16-methyl-17-cyclohexyl-18,19,20-trinorprosta-5,13-dienoic acid methyl ester Under an atmosphere of nitrogen, a solution of 2.25 g of dimethyl 2-oxo-3RS-methyl-4-cyclohexylbutylphosphonate (prepared as described in Reference Example 1) in 6 ml of tetrahydrofuran was added dropwise to a suspension of 195 mg of sodium hydride in 48 ml of tetrahydrofuran at room temperature with stirring and the mixture was stirred until the solution became clear. To the solution thus obtained was added a solution of 2.4 g of 1α-acetoxy-2α-(6-methoxycarbonylhex-cis-2-enyl)-3β-formyl-4α-(tetrahydropyran-2-yloxy)cyclopentane [prepared as described in British Patent Specification No. 1,482,928 (Example 12)] in 9 ml of tetrahydrofuran and the mixture was stirred at room temperature for 1 hour. The reaction mixture was then acidified with acetic acid and concentrated under reduced pressure. The residue was diluted with ethyl acetate, washed with water and an aqueous solution of sodium chloride, dried over magnesium sulphate and concentrated under reduced pressure. The residue was purified by column chromatography on silica gel using a mixture of cyclohexane and ethyl acetate (8:1) as eluent togive 3.0 g of the title compound having the following physical characteristics:

TLC (developing solvent, benzene:ethyl acetate =2:1): Rf=0.70;

IR (liquid film):ν; 1740, 1695, 1670, 1630, 1450, 1440, 1380, 1250, 1030, 975 cm⁻¹;

NMR (CDCl₃ solution): δ; 6.93-6.60 (1H, m), 6.40-6.17 (1H, m), 5.42-5.15 (2H, m), 5.20-5.00 (1H, m), 4.65-4.47 (1H, m), 4.20-3.30 (3H, m), 3.66 (3H, s), 2.30 (2H, t), 2.06 (3H, s), 1.09 (3H, d).

REFERENCE EXAMPLE 3

(5Z,13E)-(9α,11α,15S,16RS)-9-Acetoxy-11-(tetrahydropyran-2-yloxy)-15-hydroxy-16-methyl-17-cyclohexyl-18,19,20-trinorprosta-5,13-dienoic acid methyl ester To a solution of 3.0 g of (5Z,13E)-(9α,11α,16RS)-9-acetoxy-11-(tetrahydropyran-2-yloxy)-15-oxo-16-methyl-17-cyclohexyl-18,19,20-trinorprosta-5,13-dienoic acid methyl ester (prepared as described in Reference Example 2) in 53 ml of methanol was added portionwise 1.12 g of sodium borohydride at −30° C. After 30 minutes of stirring at −40° to −30° C., the reaction mixture was acidified with acetic acid and concentrated under reduced pressure. The residue was diluted with ethyl acetate, washed with water, an aqueous solution of sodium bicarbonate, water and an aqueous solution of sodium chloride, dried over magnesium sulphate and concentrated under reduced pressure. The residue was purified by column chromatography on silica gel using a mixture of methylene chloride and ethyl acetate (7:1) as eluent togive 1.50 g of the title compound and 1.3 g of its 15R-hydroxy isomer. The title compound showed the following physical characteristics:

TLC (developing solvent, methylene chloride:ethyl actate =2:1): Rf=0.66, (15R-hydroxy isomer, Rf =0.80):

IR (liquid film):ν; 3450, 1740, 1450, 1440, 1380, 1250, 1030, 975 cm⁻¹;

NMR (CDCl₃ solution): δ; 5.67-5.50 (2H, m), 5.43-5.27 (2H, m), 5.15-4.98 (1H, m), 4.72-4.50 (1H, m), 4.07-3.70 (3H, m), 3.57-3.27 (1H, m), 3.66 (3H, s), 2.30 (2H, t), 2.05 (3H, s).

REFERENCE EXAMPLE 4

(2-Bromoethyl)cyclohexane

To a solution of 10 g of (2-hydroxyethyl)cyclohexane in 50 ml of dry diethyl ether was added dropwise a solution of 9.85 g of phosphorous tribromide in 20 ml of dry diethyl ether at −40° C., and the mixture was stirred at −40° to −10° C. for 30 minutes and at 2° to 4° C. for 2.5 hours. The reaction mixture was then poured into ice-water and extracted with diethyl ether. The extract was washed with water, an aqueous solution of sodium bicarbonate and water, dried over magnesium sulphate and concentrated under reduced pressure. To the residue thus obtained were added 50 ml of 47% w/v hydrobromic acid at −30° C. 20 ml of sulphuric acid were then added dropwise at the same temperature. The reaction mixture was refluxed at 100° to 110° C. for 3 hours and extracted with diethyl ether. The extract was washed with water, an aqueous solution of sodium bicarbonate and water, dried over magnesium sulphate and concentrated under reduced prssure. The residue was purified by distillation under reduced pressure to give 8.04 g of the title compound having the following physical characteristics:

boiling point: 74°-74.5° C/6 mmHg;

IR (liquid film):ν; 3900, 3850, 1440, 1250, 640 cm⁻¹;

NMR (CDCl₃ solution): δ; 3.4 (2H, t), 2.0-0.3 (13H, m).

REFERENCE EXAMPLE 5

(5Z,13E)-(9α,11α,15S)-9-Acetoxy-11-(tetrahydropyran-2-yloxy)-15-hydroxy-17-cyclohexyl-18,19,20-trinorprosta-5,13-dienoic acid methyl ester Under an atmosphere of nitrogen, a trace amount of methyl iodide was added to a mixture of 693 mg of magnesium and 1.5 ml of dry diethyl ether at room temperature and to the mixture was added dropwise a solution of 5.43 g of (2-bromoethyl)cyclohexane (prepared as described in Reference Example 4) in 20 ml of dry diethyl ether. The mixture was refluxed with stirring for 2.5 hours. The Grignard reagent solution thus obtained was added dropwise to a solution of 2.0 g of 1α-acetoxy-2α-(6-methoxycarbonylhex-cis-2-enyl)-3β-(2-formyl-trans-vinyl)-4α-(tetrahdropyran-2-yloxy)cyclopentane (prepared as described in British Patent Specification No. 1,488,141) in 90 ml of dry diethyl ether at −13° to −5° C. and the mixture was stirred at the same temperature for 1.5 hours. The reaction mixture was poured into an aqueous solution of ammonium chloride and extracted with diethyl ether. The extract was washed with water and an aqueous solution of sodium chloride, dried over magnesium sulphate and concentrated under reduced pressure. The residue was purified by column chromatography on silica gel using a mixture of methylene chloride and ethyl acetate (8:1) as eluent to give 564 mg of the title compound having the following physical characteristic:

TLC (developing solvent, methylene chloride:ethyl acetate=6:1): Rf=0.45, (15R-hydroxy isomer, Rf=0.56).

The following compound was prepared by the same procedure as described above, replacing the (2-bromoethyl)-cyclohexane by cyclohexylmethyl bromide.

(a) (5Z,13E)-(9α,11α,15S)-9-Acetoxy-11-(tetrahydropyran-2-yloxy)-15-hydroxy-16-cyclohexyl-17,18,19,20-tetranorprosta-5,13-dienoic acid methyl ester, having the following physical characteristics.

TLC (developing solvent, methylene chloride:ethyl acetate=2:1): Rf=0.55 (15R-hydroxy isomer, Rf=0.71); IR (liquid film): $\nu$=3450, 1740, 1245, 1025, 975 cm$^{-1}$; NMR (CDCl$_3$ solution): $\delta$=5.70-5.48 (2H, m), 5.45-5.27 (2H, m), 5.20-4.97 (1H, m), 4.70-4.50 (1H, m), 4.28-3.28 (4H, m), 3.64 (3H, s), 2.03 (3H, s).

REFERENCE EXAMPLE 6

(5Z,13E)-(9α,11α,15S,16RS)-9-Acetoxy-11,15-bis(tetrahydropyran-2-yloxy)-16-methyl-17-cyclohexyl-18,19,20-trinorprosta-5,13-dienoic acid methyl ester To a solution of 1.50 g of (5Z,13E)-9α,11α,15S,16RS)-9-acetoxy-11-(tetrahydropyran-2-yloxy)-15-hydroxy-16-methyl-17-cyclohexyl-18,19,20-trinorprosta-5,13-dienoic acid methyl ester (prepared as described in Reference Example 3) in 35 ml of methylene chloride were added a trace amount of p-toluensulphonic acid and 345 mg of 2,3-dihydropyran at 0° C. and the mixture was stirred at 0° to 5° C. for 40 minutes. The reaction mixture was diluted with 200 ml of ethyl acetate, washed with water, an aqueous solution of sodium bicarbonate, water and an aqueous solution of sodium chloride, dried over magnesium sulphate and concentrated under reduced pressure to give 1.72 g of the title compound having the following physical characteristics:

TLC (developing solvent, benzene-ethyl acetate=2:1):Rf=0.71;

IR (liquid film):$\nu$; 1740, 1450, 1440, 1380, 1250, 1020, 975 cm$^{-1}$;

NMR (CDCl$_3$ solution): $\delta$; 5.70-5.20 (4H, m), 5.15-4.90 (1H, m), 4.80-4.50 (2H, m), 4.20-3.20 (6H, m), 3.65 (3H, s), 2.00 (3H, s).

The following compounds were prepared by the same procedure as described above.

(a) (5Z,13E)-(9α,11α,15S)-9-Acetoxy-11,15-bis-(tetrahydropyran-2-yloxy)-17-cyclohexyl-18,19,20-trinorprosta-5,13-dienoic acid methyl ester, having the following physical characteristic, was prepared from (5Z,13E)-(9α,11α,15S)-9-acetoxy-11-(tetrahydropyran-2-yloxy)-15-hydroxy-17-cyclohexyl-18,19,20-trinorprosta-5,13-dienoic acid methyl ester (prepared as described in Reference Example 5).

TLC (developing solvent, methylene chloride:ethyl acetate=3:1): Rf=0.46.

(b) (5Z,13E)-(9α,11α,15S)-9-Acetoxy-11,15-bis-(tetrahydropyran-2-yloxy)-16-cyclophexyl-17,18,19,20-tetranorprosta-5,13-dienoic acid methyl ester, having the following physical characteristics, was prepared from (5Z,13E)-(9α,11α,15S)-9-acetoxy-11-(tetrahydropyran-2-yloxy)-15-hydroxy-16-cyclohexyl-17,18,19,20-tetranorprosta-5,13-dienoic acid methyl ester [prepared as described in Reference Example 5(a)]. TLC (developing solvent, benzene:ethyl acetate=2:1):Rf=0.75;

IR (liquid film):$\nu$; 1740, 1250, 1135, 1080, 1025, 980 cm$^{-1}$;

NMR (CDCl$_3$ solution):$\delta$; 5.7-5.2 (4H, m), 5.2-4.4 (3H, m), 4.4-3.0 (6H, m), 3.65 (3H, s), 2.05 (3H, s).

REFERENCE EXAMPLE 7

(5Z,13E)-(9α,11α,15S,16RS)-9-Hydroxy-11,15-bis(tetrrhydropyran-2-yloxy)-16-methyl-17-cyclohexyl-18,19,20-trinorprosta-5,13-dienoic acid methyl ester A solution of 1.70 g of (5Z,13E)-(9α,11α,15S,16RS)-9-acetoxy-11,15-bis(tetrahydropyran-2-yloxy)-16-methyl-17-cyclohexyl-18,19,20-trinorprosta-5,13-dienoic acid methyl ester (prepared as described in Reference Example 6) in 14 ml of dry methanol was stirred with 1.44 g of anhydrous potassium carbonate at 40° C., for one hour, then cooled to 0° C., and acidified with acetic acid. The reaction mixture was diluted with ethyl acetate, washed with an aqueous solution of sodium bicarbonate and an aqueous solution of sodium chloride, dried over magneisum sulphate and concentrated under reduced pressure to give 1.55 g of the title compound having the following physical characteristics:

TLC (developing solvent, benzene-ethyl acetate=2:1):Rf=0.50;

IR (liquid film):$\nu$; 3450, 1740, 1440, 1150, 1025, 975 cm$^{-1}$;

NMR (CDCl$_3$ solution): $\delta$; 5.60-5.30 (4H, m), 4.74-4.60 (2H, m), 4.20-3.30 (7H, m), 3.65 (3H, s).

The following compounds were prepared by the same procedure as described above.

(a) (5Z,13E)-(9α,11α,15S)-9-Hydroxy-11,15-bis-(tetrahydropyran-2-yloxy)-17-cyclohexyl-18,19,20-trinorprosta-5,13-dienoic acid methyl ester, having the following physical characteristic, was prepared from (5Z,13E)-(9α,11α,15S)-9-acetoxy-11,15-bis(tetrahydropyran-2-yloxy)-17-cyclohexyl-18,19,20-trinorprosta-5,13-dienoic acid methyl ester [prepared as described in Reference Example 6(a)].

TLC (developing solvent, methylene chloride-ethyl acetate=5:1):Rf=0.11.

(b) (5Z,13E)-(9α,11α,15S)-9-Hydroxy-11,15-bis(tetrahydropyran-2-yloxy)-16-cyclohexyl-17,18,19,20-tetranorprosta-5,13-dienoic acid methyl ester, having the following physical characteristics, was prepared from (5Z,13E)-(9α,11α,15S)-9-acetoxy-11,15-bis(tetrahydropyran-2-yloxy)-16-cyclohexyl-17,18,19,20-tetranorprosta-5,13-dienoic acid methyl ester [prepared as described in Reference Example 6(b)].

TLC (developing solvent, benzene:ethyl acetate=2:1): Rf=0.45;

IR (liquid film): $\nu$; 3460, 1740, 1140, 1080, 1025, 980 cm$^{-1}$;

NMR (CDCl$_3$ solution): $\delta$; 5.60-5.20 (4H, m), 4.75-4.50 (2H, m), 4.30-3.20 (7H, m), 3.55 (3H, s).

REFERENCE EXAMPLE 8

(5Z,13E)-(9α,11α,15S,16RS)-9,11,15-Trihydroxy-16-methyl-17-cyclohexyl-18,19,20-trinorprosta-5,13-dienoic acid methyl ester 1.04 g of (5Z,13E)-(9α,11α,15S,16RS)-9-hydroxy-11,15-bis(tetrahydropyran-2-yloxy)-16-methyl-17-cyclohexyl-18,19,20-trinorprosta-5,13-dienoic acid methyl ester (prepared as described in Reference Example 7) were dissolved in a mixture of 13.2 ml of acetic acid, 4.4 ml of water and 4.4 ml of tetrahydrofuran and the mixture was stirred at 55° C. for 1 hour. The reaction mixture was added dropwise to 200 ml of a 15% w/v aqueous solution of sodium bicarbonate, and the reaction mixture was extracted with chloroform. The extract was washed with water and an aqueous solution of sodium chloride, dried over magnesium sulphate and concentrated under reduced pressure. The residue was purified by column chromatography on silica gel using a mixture of chloroform and methanol (97:3) as eluent to give 636 mg of the title compound having the following physical characteristics:

TLC (developing solvent, benzene:ethyl ether:tetrahydrofuran=1:1:1): Rf=0.31;

IR (liquid film): $\nu$; 3370, 1740, 1450, 1440, 980 cm$^{-1}$;

NMR (CDCl$_3$ solution): $\delta$; 5.75–5.20 (4H, m), 4.25–4.00 (1H, m), 4.00–3.75 (2H, m), 3.66 L (3H, s), 3.35–3.10 (2H, m).

REFERENCE EXAMPLE 9

(5E,13E)-(9α,11α,15S)-9,11,15-Trihydroxy-15-(3-propyl)cyclopentyl-16,17,18,19,20-pentanorprosta-5,13-dienoic acid methyl ester To a solution of 4.0 g of (5Z,13E)-(9α,11α,15S)-9,11,15-trihydroxy-15-(3-propyl)cyclopentyl-16,17,18,19,20-pentanorprosta-5,13-dienoic acid methyl ester [prepared as described in British Patent Application Nos. 30072/75 and 18651/76 (Example 10) and Belgian Patent No. 844256] in a mixture of 450 ml of benzene and 45 ml of methanol was added 4.0 ml of diphenyl sulphide and then the mixture was irradiated with light from a high pressure mercury lamp at room temperature for 20 hours. To the reaction mixture was added an aqueous solution of sodium carbonate and the mixture was concentrated under reduced pressure. The residue was dissolved in ethyl acetate, washed with water and an aqueous solution of sodium chloride, dried over magnesium sulphate and concentrated under reduced pressure. The residue was purified by column chromatography on silica gel pretreated with silver nitrate using a mixture of cyclohexane and ethyl acetate (1:2) as eluent to give 1.2 g of the title compound having the following physical characteristics:

TLC [developing solvent, ethyl acetate:acetic acid:methanol: isooctane:water=110:30:35:10:100 (the organic layer was used), using silica gel plate pretreated with silver nitrate]: Rf-0.42;

IR (liquid film); $\nu$; 3350, 2950, 2850, 1740, 980 cm$^{-1}$;

NMR (CDCl$_3$ solution): $\delta$; 5.7–5.2 (4H, m), 4.3–3.3 (3H, m), 3.67 (3H, s), 2.6–1.1 (24H, m), 0.95 (3H,t).

REFERENCE EXAMPLE 10

(13E)-(5RS,6RS,9α,11α,15RS,16RS)-5-Bromo-6,9-epoxy-11,15-bis(tetrahydropyran-2-yloxy)-16-cyclopentyl-18,19,20-trinorprost-13-enoic acid methyl ester Under an atmosphere of nitrogen, a solution of 620 mg of (5Z,13E)-(9α,11α-15RS,16RS)-9-hydroxy-11,15-bis(tetrahydropyran-2-yloxy)-16-cyclopentyl-18,19,20-trinorprosta-5,13-dienoic acid methyl ester [prepared by esterification of (5Z,13E)-(9α,11α,15RS,16RS)-9-hydroxy-11,15-bis(tetrahydropyran-2-yloxy)-16-cyclopentyl-18,19,20-trinorprosta-5,13-dienoic acid (prepared as described in British Patent Specification No. 1,464,916 (Example 11) using an ethereal solution of diazomethane] in a mixture of 10 ml of methylene chloride and 2 ml of N,N-dimethylformamide was added dropwise to a suspension of 215 mg of N-bromosuccinimide in 15 ml of methylene chloride at room temperature and the mixture was stirred for 30 minutes at the same temperature. The reaction mixture was then poured into ice-water and extracted with diethyl ether. The extract was washed with water and an aqueous solution of sodium chloride, dried over magnesium sulphate and concentrated under reduced pressure. The residue was purified by column chromatography on silica gel using a mixture of cyclohexane and ethyl acetate (6:1) as eluent to give 550 mg of the title compound having the following physical characteristic:

TLC (developing solvent, cyclohexane:ethyl acetate=2:1): Rf=0.56.

The following compounds were prepared by the same procedure as described above.

(a) (13E)-(15RS,6RS,9α,11α,15S)-5-Bromo-6,9-epoxy-11,15-bis(tetrahydropyran-2-yloxy)-15-cyclohexyl-16,17,18,19,20-pentanorprost-13-enoic acid methyl ester, having the following physical characteristic, was prepared from (5Z,13E)-(9α,11α,15S)-9-hydroxy-11,15-bis(tetrahydropyran-2-yloxy)-15-cyclohexyl-16,17,18,19,20-pentanorprosta-5,13-dienoic acid methyl ester [prepared by esterification of (5Z,13E)-(9α,1 1α,15S)-9-hydroxy-11,15-bis(tetrahydropyran-2-yloxy)-15-cyclohexyl-16,17,18,19,20-pentanorprosta-5,13-dienoic acid (prepared as described in British Patent Specification No. 1,488,141 (Reference Example 7)) using an ethereal solution of diazomethane].

TLC (developing solvent, cyclohexane:ethyl acetate=2:1): Rf=0.55.

(b) (13E)-(RS,6RS,9α,11α,15S)-5-Bromo-6,9-epoxy-11,15-bis(tetrahydropyran-2-yloxy)-15-(trans-4-ethyl)-cyclohexyl-16,17,18,19,20-pentanorprost-13-enoic acid methyl ester, having the following physical characteristics, was prepared from (5Z,13E)-(9α,11α,15S)-9-hydroxy-11,15-bis(tetrahydropyran-2-yloxy)-15-(trans-4-ethyl)cyclohexyl-16,17,18,19,20-pentanorprosta-5,13-dienoic acid methyl ester [prepared by esterification of (5Z,13E)-(9α,11α,15S)-9-hydroxy-11,15-bis(tetrahydropyran-2-yloxy)-15-(trans-4-ethyl)cyclohexyl-16,17,18,19,20-pentanorprosta-5,13-dienoic acid (prepared as described in British Patent Application No. 30072/75 and 18651/76 and Belgian Pat. No. 844256 (Example 3) using an ethereal solution of diazomethane].

TLC (developing solvent, cyclohexane:ethyl acetate=2:1):Rf=0.42;

IR (liquid film): $\nu$; 1740, 1440, 975 cm$^{-1}$.

(c) (13E)-(5RS,6RS,9α,11α,15S)-5-Bromo-6,9-epoxy-11,15-bis(tetrahydropyran-2-yloxy)-16-cyclohexyl-17,18,19,20-tetranorprost-13-enoic acid methyl ester, having the following physical characteristics, was prepared from (5Z,13E)-(9α,11α,15S)-9-hydroxy-11,15-bis(tetrahydropyran-2-yloxy)-16-cyclohexyl-17,18,19,20-tetranorprosta-5,13-dienoic acid methyl ester [prepared as described in Reference Example 7(b)].

IR (liquid film): $\nu$; 1740, 1445, 1205, 1140, 1080, 1040, 1025, 980 cm$^{-1}$;

NMR (CDCl$_3$ solution): $\delta$; 5.60–5.20 (2H, m), 4.70–4.30 (3H, m), 3.60 (3H, s), 4.30–3.20 (8H, m).

(d) (13E)-(5RS,6RS,9α,11α,15S)-5-Bromo-6,9-epoxy-11,15-bis(tetrahydropyran-2-yloxy)-17-cyclohexyl-18,19,20-trinorprost-13-enoic acid methyl ester, having the following physical characteristics, was prepared from (5Z,13E)-(9α,11α,15S)-9-hydroxy-11,15-bis(tetrahydropyran-2-yloxy)-17-cyclohexyl-18,19,20-trinorprosta-5,13-dienoic acid methyl ester [prepared as described in Reference Example 7(a)].

TLC (developing solvent, benzene:ethyl acetate=2:1): Rf=0.70;

NMR (CDCl$_3$ solution): $\delta$; 5.67–5.16 (4H, m), 4.9–4.5 (2H, m), 4.3–3.0 (11H, m), 3.0–0.7 (38H, m).

REFERENCE EXAMPLE 11

(13E)-(5RS,6RS,9α,11α,15S,16RS)-5-Bromo-6,9-epoxy-11,15-dihydroxy-16-cyclopentyl-18,19,20-trinorprost-13-enoic acid methyl ester 1 g of (13E)-(5RS,6RS,9α,11α,15RS,16RS)-5-Bromo-6,9-epoxy-11,15-bis(tetrahydropyran-2-yloxy)-16-cyclopentyl-18,19,20-trinorprost-13-enoic acid methyl ester (prepared as described in Reference Example 10) was dissolved in a mixture of 1.6 ml of tetrahydrofuran and 16 ml of 65% v/v aqueous acetic acid and the mixture was stirred at 40° to 45° C. for one hour. The reaction mixture was diluted with ethyl acetate, washed with water and an aqueous solution of sodium chloride, dried over magnesium sulphate and concentrated under reduced pressure. The residue was purified by column chromatography on silica gel using a mixture of cyclohexane and ethyl acetate (2:3) as eluent to give 220 mg of the title compound having the following physical characteristics:

TLC (developing solvent, chloroform:tetrahydrofuran:acetic acid=10:2:1): Rf=0.34 and 0.36: (15R-hydroxy isomer, Rf=0.42);

IR (liquid film): δ; 3370, 1740, 1440, 1020, 980 cm$^{-1}$;

NMR (CDCl$_3$ solution): δ; 5.55 (2H, m), 4.53 (1H, m), 4.30–3.70(4H, m), 3.68 (3H, m), 0.88 (3H, m).

The following compounds were prepared by the same procedure as described above.

(a) (13E)-(5RS,6RS,9α,11α,15S)-5-bromo-6,9-epoxy-11,15-dihydroxy-15 -cyclohexyl-16,17,18,19,20-pentanorprost-13-enoic acid methyl ester, having the following physical characteristics, was prepared from (13E)-(5RS,6RS,9α,11α, 15S)-5-bromo-6,9-epoxy-11,15-bis(tetrahydropyran-2-yloxy)-15-cyclohexyl-16,17,18,19,20-pentanorprost-13-enoic acid methyl ester [prepared as described in Reference Example 10(a)].

TLC (developing solvent, chloroform:tetrahydrocfuran:acetic acid = 10:2:1): Rf = 0.32;

IR (liquid film):); 3500, 1730, 970 cm$^{-1}$; NMR (CDCl$_3$ solution): δ; 5.75–5.25 (2H, m), 4.7–4.35 (1H, m), 4.35–3.5 (4H, m), 3.66 (3H, s), 3.5–3.1 (2H, m).

(b) (13E)-(5RS, 6RS, 9α, 11α, 15S)-5-bromo-6,9-epoxy-11,15-dihydroxy-15-(trans-4-ethyl)cyclohexyl-16,17,18,19,20-pentanorprost-13-enoic acid methyl ester, having the following physical characteristics, was prepared from (13E)-(5RS,6RS,9α,11α,15S)-5-bromo-6,9-epoxy-11,15-bis(tetrahydropyran-2-yloxy)-15-(trans-4-ethyl)cyclohexyl-16,17,18,19,20-pentanorprost-13-enoic acid methyl ester [prepared as described in Reference Example 10(b)].

TLC (developing solvent, chloroform:tetrahydrofuran:acetic acid = 10:2:1): Rf = 0.3;

IR (liquid film):ν; 3400, 1740, 1440,970 cm$^{-1}$;

NMR (CDCl$_3$ solution): δ; 5.8–5.4 (2H, m), 3.67 (3H, s), 4.65–3.5 (5H, m) 1.1–0.6 (3H, m). p (c) (13E)-(5RS,6RS,9α,11α,15S)-5-bromo-6,9-epoxy-11,15-dihydroxy-16-cyclohexyl-17,18,19,20-tetranorprost-13-enoic acid methyl ester, having the following physical characteristics, was prepared from (13E)-(5RS,6RS,9α,11α,15S)-5-bromo-6,9epxoy-11,15-bis(tetrahydropyran-2-yloxy)-16-cyclohexyl-17,18,19,20-tetranorprost-13-enoic acid methyl ester [prepared as described in Reference Example 10(c)].

TLC (developing solvent, chloroform:tetrahydrofuran:acetic acid = 10:2:1): Rf = 0.33 and 0.38;

IR (liquid film):ν; 3400, 1740, 1450, 1080, 1060, 975 cm$^{-1}$;

NMR (CDCl$_3$ solution): δ; 5.58–5.40 (2H, m), 4.60–4.40 (1H, m), 4.30–3.55 (4H, m), 3.67 (3H, s), 3.54–3.00 (2H, broad s).

(d) (13E)-(5RS,6RS,9α,11α,15S)-5-bromo-6,9-epoxy-11,15-dihydroxy-17-cyclohexyl-18,19,20-trinorprost-13-enoic acid methyl ester, having the following physical characteristics, was prepared from (13E)-(5RS,6RS,-9α,11α,15S)-5-bromo-6,9-epoxy-11,15-bis(tetrahydropyran-2-yloxy)-17-cyclohexyl-18,19,20-trinorprost -13-enoic acid methyl ester [prepared as described in Reference Example 10(d)].

TLC (developing solvent, chloroform:tetrahydrofuran:acetic acid = 10:2:1): Rf=0.22 and 0.28;

IR (liquid film): ν; 3400, 3000, 2950, 2870, 1750, 1450, 1380, 1250, 1200, 1180, 1070, 980 cm$^{-1}$;

NMR (CDCl$_3$ solution): δ; 5.65–5.4 (2H, m), 4.8–4.3 (1H, m), 4.3–3.2 (4H, m), 3.67 (3H, s), 2.7–0.7 (29H, m).

REFERENCE EXAMPLE 12

(13E)-(5RS,6RS,9α,11α,15S)-5-bromo-6,9-epoxy-11,15-dihydroxy-15-(3-propyl)cyclopentyl-16,17,18,19,20-pentanorprost-13-enoic acid methyl ester By proceeding as described in Reference Example 10, but using 1 g of N-bromosuccinimide and 1.83 g of (5Z,13E)-(9α,11α,15S)-9,11,15-trihydroxy-15-(3-propyl)-cyclopentyl-16,17,18,19,20-pentanorprosta-15,13-dienoic acid methyl ester dissolved in 50 ml of chloroform, there was obtained 0.95 g of the title compound having the following physical characteristics:

TLC (developing solvent, chloroform:tetrahydrofuran:acetic acid=10:2:1): Rf=0.48;

IR (liquid film):ν; 3400, 1735, 970 cm$^{-1}$;

NMR (CDCl$_3$ solution): δ; 5.65–5.4 (2H, m), 4.65–4.35 (1H, m), 3.67 (2H, s), 4.35–3.45 (4H, m), 3.3–2.7 (2H, m).

The following compounds were prepared by the same procedure as described above.

(a) (13E)-(5RS,6RS,9α,11α,15R)-S-Bromo-6,9-epoxy-11,15-dihydroxy-15-(1-butyl)cyclobutyl-16,17,18,19,20-pentanorprost-13-enoic acid methyl ester, having the following physical characteristics, was prepared from (5Z,13E)-(9α,11α,15R)-9,11,15-trihydroxy-15-(1-butyl)cyclobutyl-16,17,18,19,20-pentanorprosta-5,13-dienoic acid methyl ester [prepared by esterification of (5Z,13E)-(9α,11α,15R)-9,11,15-trihydroxy-15-(1-butyl)cyclobutyl-16,17,18,19,20-pentanorprosta-5,13-dienoic acid (prepared as described in British Patent Specification No. 1,484,210 (Example 23)) using an ethereal solution of diazomethane].

TLC (develping solvent, diethyl ether:benzene:tetrahydrofuran=1:1:1): Rf=0.69;

IR (liquid film):ν; 3400, 1730, 1430, 1370, 1240, 1050, 970 cm$^{-1}$;

NMR (CDCl$_3$ solution):δ; 5.65–5.50 (2H, m), 4.63–4.40 (1H, m), 4.30–3.75 (2H, m), 3.67 (3H, s), 0.91 (3H, t).

(b) (13E)-(5R,6S,9α,11α,15S)-5-bromo-6,9-epoxy-11,15-dihydroxy-15-(3-propyl)cyclopentyl-16,17,18,19,20-pentanorprost-13-enoic acid methyl ester, having the following physical characteristics, and its (5S,6R) isomer were prepared from (5E, 13E)-9α,1 1α,15S)-9,11,15-trihydroxy-15-(3-propyl)cyclopentyl-16,17,18,19,20-pentanorprosta-5,13-dienoic acid methyl ester (prepared as described in Reference Example 9). The (5R,6S) and (5S,6R) isomers were separated by column chromatography.

TLC (developing solvent, methylene chloride:tetrahydrofuran:acetic acid=10:2:1): Rf=0.49, [(5S,6R) isomer, Rf=0.46];

IR (liquid film):ν;3400, 2950, 2870, 1740, 1440, 970 cm$^{-1}$;

NMR (CDCl$_3$ solution):δ; 5.7–5.3 (2H, m), 4.5–4.25 (1H, m), 4.25–3.5 (4H, m), 3.67 (3H, s), 2.7–1.05 (24H, m), 0.89 (3H, m).

EXAMPLE 1

(13E)-(5RS,6RS,9α,11α,15S,16RS)-5-iodo-6,9-epoxy-11,15-dihydroxy-16-methyl-17-cyclohexyl-18,19,20-trinorprost-13-enoic acid methyl ester To a solution of 636 mg of (5Z,13E)-(9α, 11α, 15S, 16RS)-9,11,15-trihydroxy-16-methyl-17-cyclohexyl-18,19,20-trinorprosta-5,13-dienoic acid methyl ester (prepared as described in Reference Example 8) in 8.0 ml of pyridine were added portionwise 1.92 g of iodine at room temperature, the mixture was stirred for 30 minutes and then an aqueous solution of sodium thiosulphate was added to the reaction mixture. The reaction was concentrated under reduced pressure and the residue was extracted with chloroform. The extract was washed with an aqueous solution of cupric sulphate, dried over sodium sulphate and concentrated under reduced pressure. The residue was purified by column chromatography on silica gel using a mixture of cylohexane and ethyl acetate (1:1) as eluent to give 582 mg of the title compound having the following physical characteristics:

TLC (developing solvent, benzene:diethyl ether:tetrahydrofuran=1:1:1): Rf=0.51;

IR (liquid film):ν; 3370, 1740, 1450, 975 cm$^{-1}$;

NMR (CDCl$_3$ solution(: δ; 5.62–5.43 (2H, m), 4.70–4.40 (1H, m), 4.40–3.50 (4H, m), 3.66 (3H, s).

EXAMPLE 2

(5Z,13E)-(9α,11α,15S,16RS)-6,9-Epoxy-11,15-dihydroxy-16-cyclopentyl-18,19,20-trinorprosta-5,13-dienoic acid methyl ester (16-cyclopentyl-18,19,20-trinor-PGI$_2$ methyl ester)

Under an atmosphere of nitrogen, a solution of 220 mg of (13E)-(5RS,9α,11α,15S, 16RS)-5-bromo-6,9-epoxy-11,15-dihydroxy-16-cyclopentyl-18,19,20-trinorprost-13-enoic acid methyl ester (prepared as described in Reference Example 11) and 0.6 ml of DBU (1,5-diazabicyclo[5.4.0]undecene-5) was stirred at 45° to 50° C. for 1.5 hours, and then cooled to 0° to 5° C. To the reaction mixture were added 3.4 ml of 1N hydrochloric acid and 3.4 ml of phosphate buffer solution (pH 6.86)with cooling to 0° to 5° C. The reaction mixture was extracted quickly with diethyl ether. The extract was dried over magnesium sulphate and concentrated under reduced pressure at a temperature below 0° C. The residue was purified, under an atmosphere of nitrogen at 0° to 5° C., by column chromatography on Florisil (an activated magnesium siliate: "Florisil" is a registered Trade Mark of Florin Co.) using a mixture of ethyl acetate and n-hexane (1:1) containing a trace of triethylamine as eluent to give 122 mg of the title compound as a white wax having the following physical characteristics:

TLC (developing solvent, diethyl ether:acetone=3.1, using a silica gel plate pretreated with a 5% v/v solution of triethylamine in diethyl ether): Rf=0.46; IR (liquid film): ν; 3400, 1730, 1695, 1440, 1170, 1050, 975 cm$^{-1}$;

NMR (CDCl$_3$ solution): δ; 5.53 (2H, m), 4.57 (1H, m), 4.25–3.70 (3H, m), 3.65 (3H, s), 0.87 (3H, m).

The following compounds were prepared by the same procedure as described above.

(a) (5Z,13E)-(9α,11α,15S)-6,9-epoxy-11,15-dihydroxy-15-cyclohexyl-16,17,18,19,20-pentanorprosta-5,13-dienoic acid methyl ester (15-cyclohexyl-16,17,18,19,20-pentanor-PGI$_2$ methyl ester), having the following physical characteristics, was prepared from (13E)-(5RS,6RS,9α,11α,15S)-5-bromo-6,9-epoxy-11,15-dihydroxy-15-cyclohexyl-16,17,18,19,20-pentanorprost-13-enoic acid methyl ester [prepared as described in Reference Example 11(a)].

TLC (developing solvent, diethyl ether:acetone=3:1, using a silica gel plate pretreated with a 5% v/v solution of triethylamine in diethyl ether): Rf=0.58;

IR (liquid film): ν; 3430, 1740, 1715, 1695, 975 cm$^{-1}$; NMR (CDCl$_3$ solution): δ; 5.6–5.4 (2H, m), 4.7–4.4 (1H, m), 4.15 (1 H, t), 3.9–3.5 (2H, m), 3.66 (3H, s).

(b) (5Z,13E)-(9α,11α,15S)-6,9-epoxy-11,15-dihydroxy-15-(trans-4-ethyl)cyclohexyl-16,17,18,19,20-pentanorprosta-5,13-dienoic acid methyl ester [15-(trans-4-ethyl)cyclohexyl-16,17,18,19,20-pentanor-PGI$_2$ methyl ester], having the following physical characteristics, was prepared from (13E)-(5RS,6RS,9α,11α,15S)-5-bromo-6,9-epoxy-11,15-dihydroxy-15-(trans-4-ethyl)cyclohexyl-16,17,18,19,20-pentanorprost-13-enoic acid methyl ester[prepared as described in Reference Example 11(b)].

TLC (developing solvent, diethyl ether:acetone—3:1, using a silica gel plate pretreated with a 5% v/v solution of triethylamine in diethyl ether): Rf=0.53;

IR (liquid film): ν, 3350, 1730, 1700, 970 cm$^{-1}$;

NMR (CDCl$_3$ solution): δ; 5.8–5.4 (2H, m), 4.75–4.5 (1H, m), 4.35–4.05 (1H, m), 3.69 (3H, s), 4.05–3.6 (2H, m), 1.1–0.6 (3H, m).

(c) (5Z,13E)-(9α,11α,15S)-6,9-epoxy-11,15-dihydroxy-16-cyclohexyl-17,18,19,20-tetranorprosta-5,13-dienoic acid methyl ester (16-cyclohexyl-17,18,19,20-tetranor-PGI$_2$ methyl ester), having the following physical characteristics, was prepared from (13E)-(5RS,6RS,9α,11α,15S)-5-bromo-6,9-epoxy-11,15-dihydroxy-16-cyclohexyl-17,18,19,20-tetranorprost-13-enoic acid methyl ester [prepared as described in Reference Example 11(c)].

TLC (developing solvent, ethyl acetate, using a silica gel plate pretreated with a 5% v/v solution of triethylamine in ethyl acetate): Rf=0.22;

IR (liquid film): ν; 3400, 1740, 1695, 1440, 1170, 1050, 975 cm$^{-1}$;

NMR (CCl$_4$ solution): δ; 5.60–5.35 (2H, m), 4.70–4.45 (1H, m), 4.24–3.55 (3H, m), 3.68 (3H, s).

(d) (5Z,13E)-(9α,11α,15S)-6,9-epoxy-11,15-dihydroxy-17-cyclohexyl-18,19,20-trinorprosta-5,13-dienoic acid methyl ester (17-cyclohexyl-18,19,20-trinor-PGI$_2$ methyl ester), having the following physical characteristics, was prepared from (13E)-(5RS,6RS,9α,11α,15S)-5-bromo-6,9-epoxy-11,15-dihydroxy-17-cyclohexyl-18,19,20-trinorprost-13-enoic acid methyl ester [prepared as described in Reference Example 11(d)].

TLC (developing solvent, diethyl ether:acetone=3:1, using a silica gel plate pretreated with a 5% v/v solution of triethylamine in diethyl ether: Rf=0.42;

IR (liquid film): ν; 3350, 2950, 2850, 1745, 1695, 1450, 1250, 1050, 970 cm$^{-1}$;

NMR (CDCl₃ solution): δ; 5.6–5.4 (3H, m), 4.7–4.4 (1H, m), 4.3—3.5 (2H, m), 3.66 (3H, s), 3.0–0.6 (29H, m).

(e) (5Z,13E)-(9α,11α,15S)-6,9-epoxy-11,15-dihydroxy-15-(3-propyl)cyclopentyl-16,17,18,19,20-pentanorprosta-5,13-dienoic acid methyl ester [15-(3-propyl)-cyclopentyl-16,17,18,19,20-pentanor-PGI₂ methyl ester], having the following physical characteristics, was prepared from (13E)-(5RS,6RS,9α,11α,15S)-5-bromo-6,9-epoxy-11,15-dihydroxy-15-(3-propyl)cyclopentyl-16,17,18,19,20-pentanorprost-13-enoic acid methyl ester (prepared as described in Reference Example 12).

TLC (developing solvent, diethyl ether: acetone=3:1, using a silica gel plate pretreated with a 5% v/v solution of triethylamine in diethyl ether): Rf=0.45;

IR (liquid film): ν; 3400, 1740, 1715, 1695, 970 cm⁻¹;

NMR (CDCl₃ solution): δ; 5.65–5.45 (2H, m), 4.7–4.5 (1H, m), 4.17 (1H, t), 3.68 (3H, s), 4.0–3.5 (2H, m).

(f) (5Z,13E)-(9α,11α,15R)-6,9-epoxy-11,15-dihydroxy-15-(1-butyl)cyclobutyl-16,17,18,19,20-pentanorprosta-5,13-dienoic acid methyl ester [15-(1-butyl)cyclobutyl-16,17,18,19,20-pentanor-PGI₂ methyl ester], having the following physical characteristics, was prepared from (13E)-(5RS,6RS,-9α,11α,15R-(5-bromo-6,9-epoxy-11,15-dihydroxy-15-(1-butyl)cyclobutyl-16,17,18,19,20-pentanorprost-13-enoic acid methyl ester [prepared as described in Reference Example 12(a)].

TLC (developing solvent, diethyl ether:acetone=3:1, using a silica gel plate pretreated with a 5% v/v solution of triethylamine in diethyl ether): Rf=0.40;

IR (liquid film): ν, 3400, 1740, 1695, 1400, 1240, 1170, 970 cm⁻¹;

NMR (CDCl₃ solution): δ; 5.64–5.47 (2H, m), 4.67–4.45 (1H, m), 4.25–3.70 (3H, m), 3.64 (3H, s), 0.90 (3H, t).

(g) (5E,13E)-(9α,11α,15S)-6,9-epoxy-11,15-dihydroxy-15-(3-propyl)cyclopentyl-16,17,18,19,20-pentanorprosta-5,13-dienoic acid methyl ester [(5E)-15-(3-propyl)cyclopentyl-16,17,18,19,20-pentanor-PGI₂ methyl ester], having the following physicalcharacteristics, was prepared from (13E)-(5R,6S,9α,11α,15S)-5-bromo-6,9-epoxy-11,15-dihydroxy-15-(3-propyl)cyclopentyl-16,17,18,19,20-pentanorprost-13-enoic acid methyl ester [prepared as described in Reference Example 12(b)].

TLC (developing solvent, diethyl ether:acetone=3:1, using a silica gel plate pretreated with a 5% v/v solution of triethylamine in diethyl ether): Rf=0.39;

IR (liquid film): ν; 3400, 1730, 1685, 970 cm⁻¹;

NMR (CDCl₃ solution): δ; 5.8–5.4 (2H, m), 4.63 (1H, t), 4.65–4.3 (1H, m), 4.2–3.7 (2H, m), 3.62 (3H, s), 2.7–1.1 (24H, m), 0.90 (3H, m).

(h) (5Z,13E)-(9α,11α,15S,16RS)-6,9-epoxy-11,15-dihydroxy-16-methyl-17-cyclohexyl-18,19,20-trinorprosta-5,13-dienoic acid methyl ester [16RS-methyl-17-cyclohexyl-18,19,20-trinor-PGI₂ methyl ester], having the following physical characteristics, was prepared from (13E)-(5RS,6RS,9α,11α,15S,-16RS)-5-iodo-6,9-epoxy-11,15-dihydroxy-16-methyl-17-cyclohexyl-18,19,20-trinorprost-13-enoic acid methyl ester (prepared as described in Example 1).

TLC (developing solvent, ethyl acetate, using a silica gel plate pretreated with a 5% v/v solution of triethylamine in ethyl acetate): Rf=0.32;

IR (liquid film): ν; 3400, 1740, 1715, 1690, 1440, 1240, 1080, 970 cm⁻¹;

NMR (CCl₄ solution): δ; 5.73–5.20 (2H, m), 4.55–4.43 (1H, m), 4.25–3.58 (5H, m), 3.67 (3H, s).

EXAMPLE 3

(5Z,13E)-(9α,11α,15S)-6,9-epoxy-11,15-dihydroxy-15-(3-propyl)cyclopentyl-16,17,18,19,20-pentanorprosta-5,13-dienoic acid sodium salt
[15-(3-propyl)cyclopentyl-16,17,18,19,20-pentanor-PGI₂ sodium salt]

To 74 mg of 15-(3-propyl)cyclopentyl-16,17,18,19,20-pentanor-PGI₂ methyl ester [prepared as described in Example 2(e)] was added 0.69ml of a sodium hydroxide solution (prepared by dissolving 400 mg of sodium hydroxide in 2.5 ml of water and then adding to the mixture sufficient methanol to give 50 ml of solution) and the mixture was stirred at room temperature for 20 hours and then concentrated under reduced pressure. To the crystalline residue was added an adequate amount of acetone. The mixture obtained was separated by centrifugation, and the amorphous powder was dried under reduced pressure to give 74 mg of the title compound having the following physical characteristics:

IR (KBr tablet): ν; 3350, 1695, 1560, 970 cm⁻¹;

NMR [CD₃OD+benzene solution]: δ; 5.65–5.45 (2H, m), 4.65–4.4 (1H, m) 4.3–4.0 (1H, m), 4.0–3.6 (2H, m), 1.05–0.6 (3H, m).

EXAMPLE 4

β-Cyclodextrin clathrate of
(5Z,13E)-(9α,11α,15S)-6,9-epoxy-11,15-dihydroxy-15-(3-propyl)cyclopentyl-16,17,18,19,20-pentanorprosta-5,13-dienoic acid methyl ester [or β-cyclodextrin clathrate of
15-(3-propyl)cyclopentyl-16,17,18,19,20-pentanor-PGI₂ methyl ester]

A solution of 5.60 mg of (5Z,13E)-9α,11α,15S)-6,9-epoxy-11,15-dihydroxy-15-(3-propyl)cyclopentyl-16,17,18,19,20-pentanorprosta-5,13-dienoic acid methyl ester [prepared as described in Example 2(e)] in 1.5 ml of ethanol was added to a solution of 74.32 mg of β-cyclodextrin in 3 ml of a 1% v/v solution of triethylamine in water, and the mixture was stirred at room temperature for 5 minutes. The mixture was concentrated under reduced pressure to give 72.39 mg of the β-cyclodextrin clathrate of the compound specified in the title. The content of prostaglandin analog in the product was 7.7% by weight.

EXAMPLE 5

α-Cyclodextrin clathrate of
(5Z,13E)-(9α,11α,15S)-6,9-epoxy-11,15-dihydroxy-15-(3-propyl)cyclopentyl-16,17,18,19,20-pentanorprosta-5,13-dienoic acid methyl ester [or α-cyclodextrin clathrate of
15-(3-propyl)cyclopentyl-16,17,18,19,20-pentanor-PGI₂ methyl ester]

By proceeding as described in Example 4, but replacing the β-cyclodextrin by 186.23 mg of α-cyclodextrin dissolved in 2 ml of a 1% v/v solution of triethylamine in water and utilizing a solution of 5.49 mg of (5Z,13E)-(9α,11α,15S)-6,9-epoxy-11,15-dihydroxy-15-(3-propyl)-cyclopentyl-16,17,18,19,20-pentanorprosta-5,13-dienoic acid methyl ester [prepared as described in Example 2(e)] in 1.5 ml of ethanol, there were obtained 166.30 mg of the α-cyclodextrin clathrate of the compound specified in the title. The content of prostaglandin analogue in the product was 3.2% by weight.

The present invention includes within its scope pharmaceutical compositions which comprise at least one new therapeutically useful compound of general formula II, or cyclodextrin clathrate or non-toxic salt thereof, together with a pharmaceutical carrier or coating. In clinical practice the new compounds of the present invention will normally be administered parenterally, vaginally or rectally.

Preparations according to the invention for parenteral administration include sterile aqueous or nonaqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

Solid compositions for vaginal administration include pessaries formulated in maner known per se and containing one or more of the active compounds.

Solid compositions for rectal administration include suppositories formulated in manner known per se and containing one or more of the active compounds.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection. The dose employed depends upon the desired therapeutic effect, the route of administration and the duration of the treatment.

In the human adult, each dose per person is generally between 0.05 and 500 μg by parenteral administration in the treatment of hypertension, between 0.05 and 500 μg by parenteral administration in the treatment of disorders of the peripheral circulation, and between 0.05 and 500 μg by parenteral administration in the prevention and treatment of cerebral thrombosis, myocardial infarction and arteriosclerosis.

The following Example illustrates pharmaceutical compositions according to the invention.

EXAMPLE 6

(5Z,13E)-(9α,11α,15S)-6,9-epoxy-11,15-dihydroxy-15-(3-propyl)cyclopentyl-16,17,18,19,20-pentanorprosta-5,13-dienoic acid methyl ester (500 μg) was dissolved in ethanol (5ml). The solution was then sterilized by passage through a bacteria-retaining filter and placed in 0.1 ml portions in 1 ml ampoules, to give 10 μg of (5Z,13E)-(9α,11α,15S)-6,9-epoxy-11,15-dihydroxy-15-(3-propyl)cyclopentyl-16,17,18,19,20-pentanorprosta-5,13-dienoic acid methyl ester per ampoule. The ampoules were sealed. The contents of an ampoule diluted to a suitable volume, e.g. with 1 ml of tris-HCl-buffer solution (pH 8.6), gave a solution ready for administration by injection.

We claim:

1. A prostaglandin of the formula:

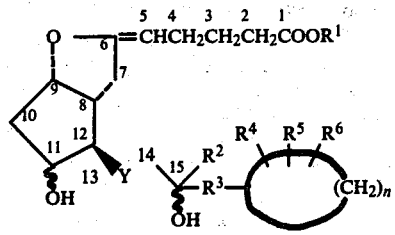

wherein Y is trans-vinylene or ethylene, $R^1$ is hydrogen or straight- or branched-chain alkyl of from 1 to 12 carbon atoms, $R^2$ is hydrogen, methyl, or ethyl, $R^3$ is a single bond, or straight- or branched-chain alkylene of from 1 to 4 carbon atoms, $R^4$, $R^5$ and $R^6$, which may be the same or different, are each hydrogen, or straight- or branched-chain alkyl of from 1 to 8 carbon atoms, n is 3, 4, 5, or 6, the wavy line attached to the carbon atoms in positions 11 and 15 depicted in the formula show that the perspective hydroxyls attached to the said positions have the α- or β-configuration or a mixture thereof, and the double bond between $C_5$–$C_6$ is Z or E and, when $R^1$ is hydrogen, non-toxic salts thereof.

2. A prostaglandin according to claim 1 wherein the double bond between $C_5$–$C_6$ is Z and, when $R^1$ is hydrogen, non-toxic salts thereof.

3. A prostaglandin according to claim 1 wherein the double bond between $C_5$–$C_6$ is E and, when $R^1$ is hydrogen, non-toxic salts thereof.

4. A prostaglandin according to claim 1 wherein Y is trans-vinylene and, when $R^1$ is hydrogen, non-toxic salts thereof.

5. A prostaglandin according to claim 1 wherein $R^1$ is hydrogen atom or straight- or branched chain alkyl from 1 to 4 carbon atoms and, when $R^1$ is hydrogen, non-toxic salts thereof.

6. A prostaglandin according to claim 1 wherein $R^1$ is methyl.

7. A prostaglandin according to claim 1 wherein $R^2$ is hydrogen and, when $R^1$ is hydrogen, non-toxic salts thereof.

8. A prostaglandin according to claim 1 wherein $R^4$, $R^5$ and $R^6$ are each hydrogen or one of $R^4$, $R^5$ and $R^6$ is alkyl of from 1 to 4 carbon atoms and the other two are hydrogen, and, when $R^1$ is hydrogen, non-toxic salts thereof.

9. A prostaglandin according to claim 1 wherein the grouping

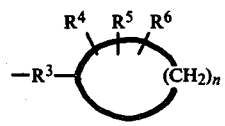

in the formula depicted in claim 1 is cyclobutyl, (1-propyl)cyclobutyl, (1-butyl)cyclobutyl, (1-pentyl)cyclobutyl, (1-hexyl)cyclobutyl, (2-propyl)cyclobutyl, (3-ethyl)cyclobutyl, (3-propyl)cyclobutyl, cyclopentyl, cyclopentylmethyl, 1-cyclopentylethyl, 2-cyclopentylethyl, 2-cyclopentylpropyl, (3-ethyl)cyclopentyl, (3-propyl)cyclopentyl, (3-butyl)cyclopentyl, (1-methyl-3-propyl)cyclopentyl, (2-methyl-3-propyl)cyclopentyl, (2-methyl-4-propyl)cyclopentyl, cyclohexyl, cyclohexylmethyl, 1-cyclohexylethyl, 2-cyclohexylethyl, (1-cyclohexyl-1-methyl)ethyl, (1-methyl-2-cyclohexyl)ethyl, 2-cyclohexylpropyl, 3-cyclohexylpropyl, (3-ethyl)cyclohexyl, (4-methyl)cyclohexyl, (4-ethyl)cyclohexyl, (4-propyl)cyclohexyl, (2,6-dimethyl)cyclohexyl, (2,6-dimethyl-4-propyl)cyclohexyl, (1-methylcyclohexyl)methyl, cycloheptyl or 1-cycloheptylethyl and, when R¹ is hydrogen, non-toxic salts thereof.

10. A prostaglandin according to claim 1 wherein the grouping

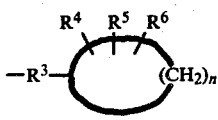

in the formula depicted in claim 1 is 1-cyclopentylethyl, cyclohexyl, (trans-4-ethyl)cyclohexyl, cyclohexylmethyl, 2-cyclohexylethyl, (3-propyl)cyclopentyl, (1-butyl)cyclobutyl or (1-methyl-2-cyclohexyl)ethyl and, when R¹ is hydrogen, non-toxic salts thereof.

11. A prostaglandin according to claim 1 which is (5Z, 13E)-(9α,11α,15S,16RS)-6,9-epoxy-11,15-dihydroxy-16-cyclopentyl-18,19,20-trinorprosta-5,13-dienoic acid methyl ester.

12. A prostagladin according to claim 1 which is (5Z,13E)-(9α,11α,15S)-6,9-epoxy-11,15-dihydroxy-15-cyclohexyl-16,17,18,19,20-pentanorprosta-5,13-dienoic acid methyl ester.

13. A prostaglandin according to claim 1 which is (5Z,13E)-(9α,11α,15S)-6,9-epoxy-11,15-dihydroxy-15-(trans-4-ethyl)cyclohexyl-16,17,18,19,20-pentanorprosta-5,13-dienoic acid methyl ester.

14. A prostaglandin according to claim 1 which is (5Z,13E)-(9α,11α,15S)-6,9-epoxy-11,15-dihydroxy-16-cyclohexyl-17,18,19,20-tetranorprosta-5,13-dienoic acid methyl ester.

15. A prostaglandin according to claim 1 which is (5Z,13E)-(9α,11α,15S)-6,9-epoxy-11,15-dihydroxy-17-cyclohexyl-18,19,20-trinorprosta-5,13-dienoic acid methyl ester.

16. A prostaglandin according to claim 1 which is (5Z,13E)-(9α,11α,15S)-6,9-epoxy-11,15-dihydroxy-15-(3-propyl)cyclopentyl-16,17,18,19,20-pentanorprosta-5,13-dienoic acid methyl ester.

17. A prostanglandin according to claim 1 which is (5Z,13E)-(9α,11α,15R)-6,9-epoxy-11,15-dihydroxy-15-(1-butyl)cyclobutyl-16,17,18,19,20-pentanorprosta-5,13-dienoic acid methyl ester.

18. A prostaglandin according to claim 1 which is (5E,13E)-(9α,11α,15S)-6,9-epoxy-11,15-dihydroxy-15-(3-propyl)cyclopentyl-16,17,18,19,20-pentanorprosta-5,13-dienoic acid methyl ester.

19. A prostaglandin according to claim 1 which is (5Z,13E)-(9α,11α,15S,16RS)-6,9-epoxy-11,15-dihydroxy-16-methyl-17-cyclohexyl-18,19,20-trinorprosta-5,13-dienoic acid methyl ester.

20. A prostaglandin according to claim 1 which is (5Z,13E)-(9α,11α,15S)-6,9-epoxy-11,15-dihydroxy-15-(3-propyl)cyclopentyl-16,17,18,19,20-pentanorprosta-5,13-dienoic acid sodium salt.

21. A pharmaceutical antithrombotic or hypotensive composition which comprises, as active ingredient, an antithrombotic or hypotensive amount of at least one compound as claimed in claim 1 in association with a pharmaceutical carrier or coating.

* * * * *